(12) United States Patent
Ozcan et al.

(10) Patent No.: US 7,133,134 B2
(45) Date of Patent: *Nov. 7, 2006

(54) METHOD OF MEASURING A PHYSICAL FUNCTION USING A SYMMETRIC COMPOSITE FUNCTION

(75) Inventors: Aydogan Ozcan, Menlo Park, CA (US); Michel J. F. Digonnet, Palo Alto, CA (US); Gordon S. Kino, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/357,275

(22) Filed: Jan. 31, 2003

(65) Prior Publication Data

US 2004/0036880 A1    Feb. 26, 2004

Related U.S. Application Data

(60) Provisional application No. 60/405,405, filed on Aug. 21, 2002.

(51) Int. Cl.
*G01N 21/59* (2006.01)
(52) U.S. Cl. ............... 356/432; 356/614; 359/359
(58) Field of Classification Search ........ 356/432–436, 356/444, 345–346, 450–451; 359/251, 257, 359/328, 371, 359, 386; 385/122, 3; 252/587, 252/582
See application file for complete search history.

(56) References Cited

U.S. PATENT DOCUMENTS 3,880,630 A * 4/1975 Izawa ..................... 65/30.14

| 4,792,230 | A |   | 12/1988 | Naganuma et al. |
|-----------|---|---|---------|-----------------|
| 4,985,178 | A | * | 1/1991  | Tam ............................ 252/587 |
| 5,086,239 | A |   | 2/1992  | Wang            |
| 5,194,918 | A |   | 3/1993  | Kino et al.     |
| 5,220,451 | A | * | 6/1993  | Gotoh et al. ................. 359/251 |
| 5,239,407 | A | * | 8/1993  | Brueck et al. .............. 359/326 |
| 5,247,601 | A | * | 9/1993  | Myers et al. ............... 385/122 |
| 5,262,890 | A | * | 11/1993 | Berkovic et al. ........... 359/328 |
| 5,309,532 | A | * | 5/1994  | Chang et al. ................... 385/3 |
| 5,368,782 | A | * | 11/1994 | Gotoh et al. ................. 252/587 |
| 5,420,717 | A |   | 5/1995  | Tabata          |
| 5,434,699 | A | * | 7/1995  | Berkovic et al. ........... 359/328 |
| 5,481,636 | A | * | 1/1996  | Fukuda et al. .............. 385/122 |

(Continued)

FOREIGN PATENT DOCUMENTS

JP    2000 329618 A    11/2000

(Continued)

OTHER PUBLICATIONS

Ferreira, Paulo Jorge S.G., *Interpolation and the Discrete Papoulis-Gerchberg Algorithm*, IEEE Transactions on Signal Processing, vol. 42, No. 10, Oct. 1994, pp. 2596-2606.

(Continued)

*Primary Examiner*—Layla G. Lauchman
*Assistant Examiner*—Sang H. Nguyen
(74) *Attorney, Agent, or Firm*—Knobbe, Martens, Olson & Bear, LLP

(57) ABSTRACT

A method measures a physical function, such as a second-order optical nonlinearity profile, or a temporal waveform of a laser pulse. The method includes forming a symmetric composite function by superimposing the physical function with a substantially identical physical function. The method further includes obtaining a Fourier transform of the symmetric composite function. The method further includes calculating an inverse Fourier transform of the obtained Fourier transform. The calculated inverse Fourier transform provides information regarding the physical function.

21 Claims, 27 Drawing Sheets

U.S. PATENT DOCUMENTS

| | | | |
|---|---|---|---|
| 5,523,840 A * | 6/1996 | Nishizawa et al. | 356/497 |
| 5,530,544 A | 6/1996 | Trebino et al. | |
| 5,615,041 A * | 3/1997 | Field et al. | 359/326 |
| 6,043,884 A | 3/2000 | Curbelo | |
| 6,456,380 B1 * | 9/2002 | Naganuma | 356/450 |
| 6,650,466 B1 * | 11/2003 | Wise et al. | 359/328 |
| 6,856,393 B1 | 2/2005 | Ozcan et al. | |
| 2004/0044714 A1 | 3/2004 | Ozcan et al. | |
| 2004/0133614 A1 | 7/2004 | Ozcan et al. | |

FOREIGN PATENT DOCUMENTS

| | | |
|---|---|---|
| JP | 2001 083015 A | 3/2001 |
| WO | PCT/US03/26311 | 8/2003 |

OTHER PUBLICATIONS

Kashyap, Raman, et al., *Phase-matched second harmonic generation by periodic poling of fused silica*, Applied Physics Letters, vol. 64, No. 11, Mar. 14, 1994, pp. 1332-1334.

Ozcan, A., et al., *Inverse Fourier transform technique to determine second-order optical nonlinearity spatial profiles*, Applied Physics Letters, vol. 82, No. 9, Mar. 3, 2003, pp. 1362-1364.

"Invitation to Pay Additional Fees" from the International Searching Authority regarding corresponding PCT Application No. PCT/US 03/26311, filed Aug. 21, 2003, including Annex to Form PCT/ISA/206, "Communication Relating to the Results of the Partial International Search".

Qui, Mingxin, et al., *Erratum: "Double fitting of Marker fringes to characterize near-surface and bulk second-order nonlinearities in poled silica,"* Applied Physics Letters, vol. 77, No. 23, Dec. 4, 2000, p. 3863.

Alley, Thomas G., et al., *Space charge dynamics in thermally poled fused silica*, Journal of Non-Crystalline Solids 242 (1998). pp. 165-176.

Bonfrate, G., et al., *Parametric fluorescence in periodically poled silica fibers*, Applied Physics Letters, vol. 75, No. 16, Oct. 18, 1999, pp. 2356-2358.

Faccio, D., et al., *Dynamics of the second-order nonlinearity in thermally poled silica glass*, Applied Physics Letters, vol. 79, No. 17, Oct. 22, 2001, pp. 2687-2689.

Fisher, Robert A., et al., *Transient analysis of Kerr-like phase conjugators using frequency-domain techniques*, Physical Review A, vol. 23, No. 6, Jun. 1981, pp. 3071-3083.

Kazansky, P.G., et al., *Thermally poled silica glass: Laser induced pressure pulse probe of charge distribution*, Applied Physics Letters, vol. 68, No. 2, Jan. 8, 1996, pp. 269-271.

Liu, Alice C., et al., *Advances in the measurement of the poled silica nonlinear profile*, SPIE vol. 3542, Nov. 1998, pp. 115-119.

Maker, P.D., et al., *Effects of Dispersion and Focusing on the Production of Optical Harmonics*, Physical Review Letters, vol. 8, No. 1, Jan. 1, 1962, pp. 21-22.

Milane, R.P., *Analytic Properties of the Hartley Transform and their Implications*, Proceedings of the IEEE, vol. 82, No. 3, Mar. 1994, pp. 413-428.

Miller, D.A.B., *Time reversal of optical pulses by four-wave mixing*, Optic Letters, vol. 5, No. 7, Jul. 1980, pp. 300-302.

Myers, R.A., et al., *Large second-order nonlinearity in poled fused silica*, Optics Letters, vol. 16, No. 22, Nov. 15, 1991, pp. 1732-1734.

Nakajima, N., *Reconstruction of a real function from its Harley-transform intensity*, J. Opt. Soc. Am. A., vol. 5, No. 6, Jun. 1988, pp. 858-863.

Pureur, D., et al., *Absolute measurement of the second-order nonlinearity profile in poled silica*, Optics Letters, vol. 23, No. 8, Apr. 15, 1998, pp. 588-590.

Qiu, Mingxin, et al., *Double fitting of Maker fringes to characterize near-surface and bulk second-order nonlinearities in poled silica*, Applied Physics Letters, vol. 76, No. 23, Jun. 5, 2000, pp. 3346-3348.

Quiquempois, Y., et al., *Localisation of the induced second-order non-linearity within Infrasil and Suprasil thermally poled glasses*, Optics Communications 176, Apr. 1, 2000, pp. 479-487.

Sun, P.C., et al., *Femtosecond pulse imaging: ultrafest optical oscilloscope*, J. Opt. Soc. Am. A, vol. 14, No. 5, May 1997. pp. 1159-1170.

Watanabe, Shigeki et al., *Compensation of Chromatic Dispersion in a Single-Mode Fiber by Optical Phase Conjugation*. IEEE Photonics Technology Letters. vol. 5. No. 1, Jan. 1993, pp. 92-95.

Weiner. Andrew M., et al., *Femtosecond Pulse Shaping for Synthesis, Processing, and Time-to-Space Conversion of Ultrafast Optical Waveforms*. IEEE Journal of Selected Topics in Quantum Electronics. vol. 4, No. 2, Mar./Apr. 1998, pp. 317-331.

Weiner, Andrew M., et al., *Femtosecond Spectral Holography*, IEEE Journal of Quantum Electronics, vol. 28, No. 10, Oct. 1992, pp. 2251-2256.

Yariv, Amnon et al., *Compensation for channel dispersion by nonlinear optical phase conjugation*. Optics Letters, vol. 4, No. 2, Feb. 1979, pp. 52-54.

Fienup, J.R., "Reconstruction of an object from the modulus of its Fourier transform," *Optics Letters*, vol. 3, No. 1, Jul. 1978, pp. 27-29.

Ozcan, A., et al., "A simple post-processing technique to improve the retrieval accuracy of second-order nonlinearity profiles," Edward L. Ginzton Laboratory: Stanford University, Stanford, California 94305; ©2004 Optical Society of America, 2 pages.

Ozcan, A., et al., "Cylinder-assisted Maker-fringe Technique," *Electronics Letters*, vol. 39, No. 25, Dec. 11, 2003, 2 pages.

Ozcan, A., et al., "Improved Fourier transform technique to determine second-order optical nonlinearity profiles," Edward L. Ginzton Laboratory: Stanford University, Stanford, California 94305; © 2003 Optical Society of America, 3 pages.

Ozcan, A., et al., "Improved technique to determine second-order optical nonlinearity profiles using two different samples," *Applied Physics Letters*, vol. 84, No. 5, Feb. 2, 2004, pp. 681-683.

Ozcan, A., et al., Erratum: "Inverse Fourier transform technique to determine second-order optical nonlinearity spatial profiles," *Applied Physics Letters*, vol. 83, No. 8, Aug. 25, 2003, p. 1679.

Ozcan, A., et al., "Post-processing of the second-order optical nonlinearity profile of thin films," Edward L. Ginzton Laboratory: Stanford University, Stanford, California 94305; © 2004 Optical Society of America, 2 pages.

Ozcan, A., et al., "Simplified inverse Fourier transform to determine second-order optical nonlinearity profiles using a reference sample," *Electronics Letters*, vol. 40, No. 9, Apr. 29, 2004, 2 pages.

Quatieri, Thomas F., Jr., et al., "Iterative techniques for minimum phase signal reconstruction from phase or magnitude," *IEEE Trans. Acoust. Speech, Signal Processing*, vol. 29, 1981, pp. 1187-1193.

Rosenthal, Amir, et al., "Inverse Scattering Algorithm for Reconstructing Strongly Reflecting Fiber Bragg Gratings," *IEEE Journal of Quantum Electronics*, vol. 39, No. 8, Aug. 2003, pp. 1018-1026.

* cited by examiner

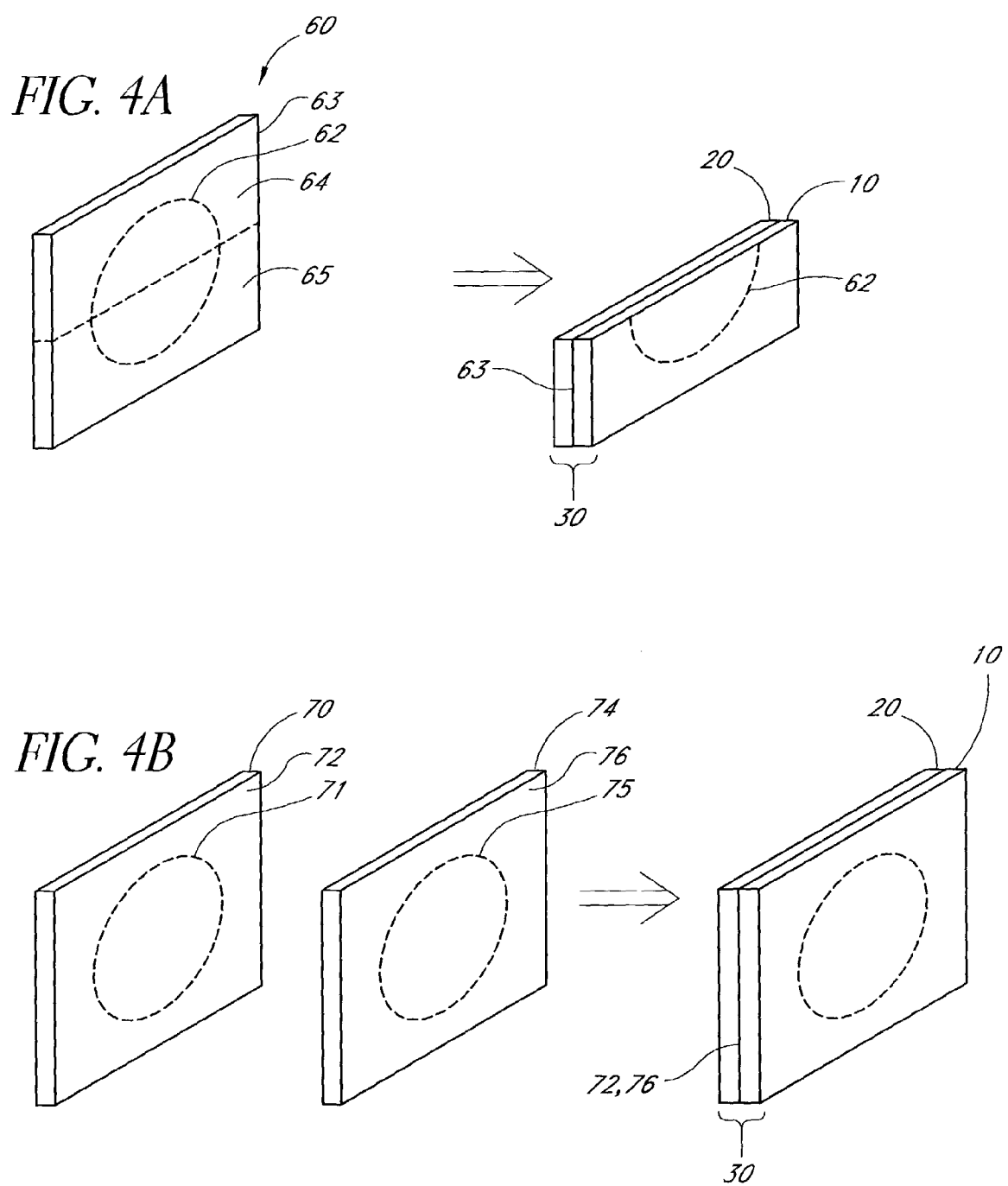

METHOD OF MEASURING A PHYSICAL FUNCTION USING A SYMMETRIC COMPOSITE FUNCTION

CLAIM PRIORITY

This application claims priority to U.S. Provisional Application No. 60/405,405, filed Aug. 21, 2002, which is incorporated by reference in its entirety herein.

BACKGROUND OF THE INVENTION

1. Field of the Invention

The present invention relates generally to the field of measuring attributes of a physical system, and more particularly to methods of measuring a non-symmetric physical function.

2. Description of the Related Art

Various optical devices are based on induced second-order susceptibilities in silica-based glass waveguides (e.g., electro-optic modulators, switches, parametric amplifiers). For example, G. Bonfrate et al. describe optical parametric oscillators useful for the study of quantum interference and quantum cryptography, and for metrology applications in *Parametric Fluorescence in Periodically Poled Silica Fibers*, Applied Physics Letters, Vol. 75, No. 16, 1999, pages 2356–2358, which is incorporated in its entirety by reference herein. Second-order susceptibility can be induced in a several-microns-thick region of fused silica (a material that is not normally centro-symmetric, and therefore normally does not exhibit a second-order susceptibility) by poling at elevated temperatures. This phenomenon has been described by R. A. Myers et al. in *Large Second-Order Nonlinearity in Poled Fused Silica*, Optics Letters, Vol. 16, No. 22, 1991, pages 1732–1734, which is incorporated in its entirety by reference herein.

FIGS. 1A and 1B schematically illustrate the poling of a silica wafer 1. As schematically illustrated in FIG. 1A, poling typically comprises using an anode electrode 2 placed in proximity to one surface 3 of the wafer 1 and a cathode electrode 4 placed in proximity to the opposite surface 5 of the wafer 1. A voltage is applied across the wafer 1 for a period of time, resulting in a second-order optical nonlinearity profile having a thickness and localized beneath the surface 3 where the anode electrode was placed, as schematically illustrated in FIG. 1B. Such a poling procedure is described in more detail by Thomas G. Alley et al. in *Space Charge Dynamics in Thermally Poled Fused Silica*, Journal of Non-Crystalline Solids, Vol. 242, 1998, pages 165–176, which is incorporated herein in its entirety.

The field of poled silica has suffered from the lack of a common method to reliably measure the second-order optical nonlinearity profile of poled samples. This absence of a reliable procedure for measuring nonlinearity profiles may be the reason, at least in part, for wide discrepancies in the measured magnitudes and the positions of the nonlinearity profiles of various poled systems as reported in the literature. The Maker fringe (MF) technique is the most common method currently used to investigate the nonlinearity profile of poled silica. The MF technique comprises focusing a pulsed laser beam of intensity $I_1$ (known as the fundamental signal) onto a sample at an incident angle $\theta$ and measuring the intensity $I_2$ of the second harmonic (SH) signal generated within the nonlinear region as a function of the incident angle $\theta$. For a transverse magnetic (TM) polarized fundamental laser beam, the conversion efficiency $\eta_{TM}(\theta)$ is given by:

$$\eta_{TM}(\theta) = \frac{I_2}{I_1} = f(\theta, n_1, n_2) \left| \int d_{33}(z) e^{j\Delta k(\theta) z} dz \right|^2 \quad (1)$$

where $d_{33}(z)$ is the nonlinear coefficient (which is proportional to the second-order susceptibility $\chi^{(2)}$);

$z$ is the direction normal to the sample surface (i.e., parallel to the poling field);

$n_1$ and $n_2$ are the refractive indices at the fundamental and SH frequencies, respectively;

$\Delta k = k_2 - 2k_1$, where $k_1$ and $k_2$ are the fundamental and SH wave numbers, respectively, and $f(\theta, n_1, n_2)$ is a well-defined function of the incident angle $\theta$ (relative to the surface normal direction) and refractive indices $n_1$ and $n_2$.

The function $f(\theta, n_1, n_2)$ accounts for both the power loss due to reflection suffered by the fundamental and the SH beams, and the projection of the input electric field along the appropriate direction. In general, $f(\theta, n_1, n_2)$ depends on both the polarization of the input fundamental wave and the geometry of the second harmonic generation configuration. The exact formula of $f(\theta, n_1, n_2)$ is given by D. Pureur, et al. in *Absolute Measurement of the Second-Order Nonlinearity Profile in Poled Silica*, Optics Letters, Vol. 23, 1998, pages 588–590, which is incorporated in its entirety by reference herein. This phenomenon is also described by P. D. Maker et al. in *Effects of Dispersion and Focusing on the Production of Optical Harmonics*, Physics Review Letters, Vol. 8, No. 1, 1962, pages 21–22, which is incorporated in its entirety by reference herein.

The conversion efficiency $\eta_{TM}(\theta)$ is obtained experimentally by rotating the sample with respect to the incident laser beam and measuring the power of the SH signal as a function of the incident angle $\theta$. Due to dispersion of the laser beam, $\Delta k$ is finite and $\eta_{TM}(\theta)$ exhibits oscillations (called the Maker fringes) which pass through several maxima and minima. The objective of this measurement is to retrieve the second-order nonlinearity profile $d_{33}(z)$. The absolute value of the integral in Equation 1 is the amplitude of the Fourier transform of $d_{33}(z)$. In principle, if one knew both the amplitude and the phase of a Fourier transform, one can readily infer the argument of the Fourier transform (in this case $d_{33}(z)$) by taking the inverse Fourier transform of the Fourier transform. However, the measured Maker fringes provide only the magnitude of the Fourier transform, not its phase. Consequently, for an arbitrary and unknown nonlinearity profile, the MF measurement alone is not sufficient to determine a unique solution for $d_{33}(z)$. Even if the phase information were available, it would provide the shape of $d_{33}(z)$ but it would still not provide the location of this shape beneath the surface of the sample (i.e., where the nonlinearity profile starts beneath the surface).

Previous efforts to determine $d_{33}(z)$ have involved fitting various trial profiles to the measured MF data. Examples of such efforts are described by M. Qiu et al. in *Double Fitting of Maker Fringes to Characterize Near-Surface and Bulk Second-Order Nonlinearities in Poled Silica*, Applied Physics Letters, Vol. 76, No. 23, 2000, pages 3346–3348; Y. Quiquempois et al. in *Localisation of the Induced Second-Order Non-Linearity Within Infrasil and Suprasil Thermally Poled Glasses*, Optics Communications, Vol. 176, 2000, pages 479–487; and D. Faccio et al. in *Dynamics of the Second-Order Nonlinearity in Thermally Poled Silica Glass*, Applied Physics Letters, Vol. 79, No. 17, 2001, pages 2687–2689. These references are incorporated in their entirety by reference herein.

However, the previous methods do not produce a unique solution for $d_{33}(z)$. Two rather different trial profiles can provide almost equally good fits to the measured MF data. This aspect of using fitting routines to determine $d_{33}(z)$ is described in more detail by Alice C. Liu et al. in *Advances in the Measurement of the Poled Silica Nonlinear Profile*, SPIE Conference on Doped Fiber Devices II, Boston, Mass., November 1998, pages 115–119, which is incorporated in its entirety by reference herein.

SUMMARY OF THE INVENTION

According to one aspect of the present invention, a method measures a second-order optical nonlinearity profile of a sample. The method comprises providing the sample having the second-order optical nonlinearity profile. The method further comprises placing a surface of the sample in proximity to a surface of a supplemental sample. The sample and supplemental sample form a composite sample having a symmetric second-order optical nonlinearity profile. The method further comprises measuring a Fourier transform of the symmetric second-order optical nonlinearity profile. The method further comprises calculating an inverse Fourier transform of the measured Fourier transform. The calculated inverse Fourier transform provides information regarding the second-order optical nonlinearity profile.

In another aspect of the present invention, a method measures a physical function. The method comprises forming a symmetric composite function by superimposing the physical function with a substantially identical physical function. The method further comprises obtaining a Fourier transform of the symmetric composite function. The method further comprises calculating an inverse Fourier transform of the obtained Fourier transform. The calculated inverse Fourier transform provides information regarding the physical function.

In still another aspect of the present invention, a method determines the temporal waveform of a laser pulse. The method comprises providing a laser pulse having a temporal waveform. The method further comprises providing a time-reversed pulse having a time-reversed temporal waveform which corresponds to the temporal waveform of the laser pulse after being time-reversed. The method further comprises forming a symmetric composite waveform by combining the temporal waveform of the laser pulse and the time-reversed temporal waveform of the time-reversed pulse. The method further comprises obtaining a Fourier transform of the symmetric composite waveform. The method further comprises calculating an inverse Fourier transform of the obtained Fourier transform. The calculated inverse Fourier transform provides information regarding the temporal waveform of the laser pulse.

For purposes of summarizing the invention, certain aspects, advantages and novel features of the invention have been described herein above. It is to be understood, however, that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIGS. 4A–4D schematically illustrate various embodiments of the supplemental sample in accordance with embodiments of the present invention.

DETAILED DESCRIPTION OF THE PREFERRED EMBODIMENT

Figure 1A:
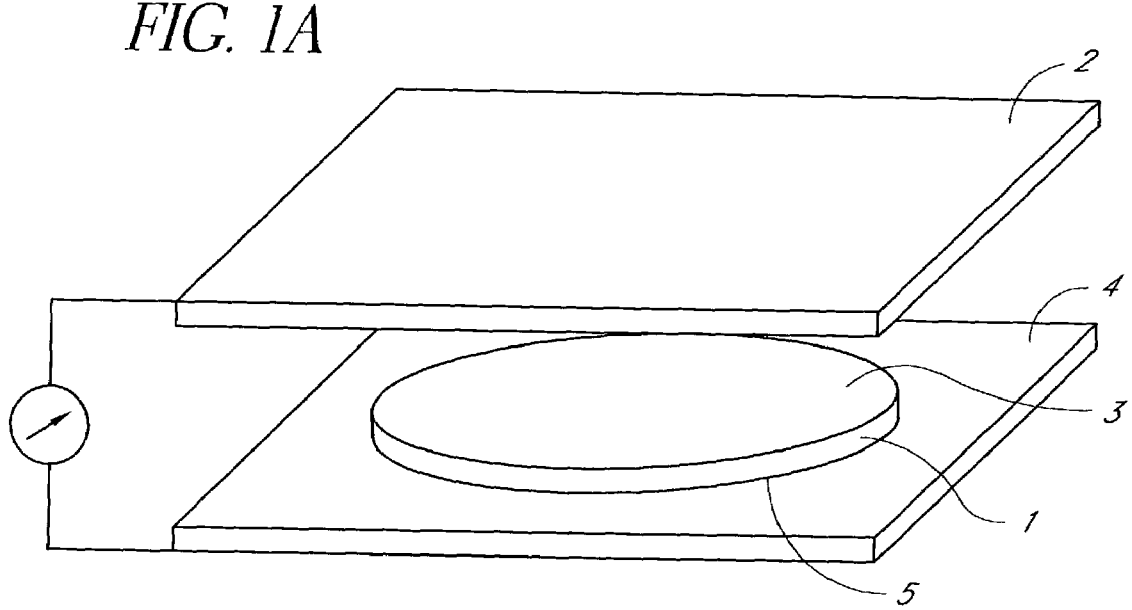
FIGS. 1A and 1B schematically illustrate the poling of a silica wafer.
Figure 1B:
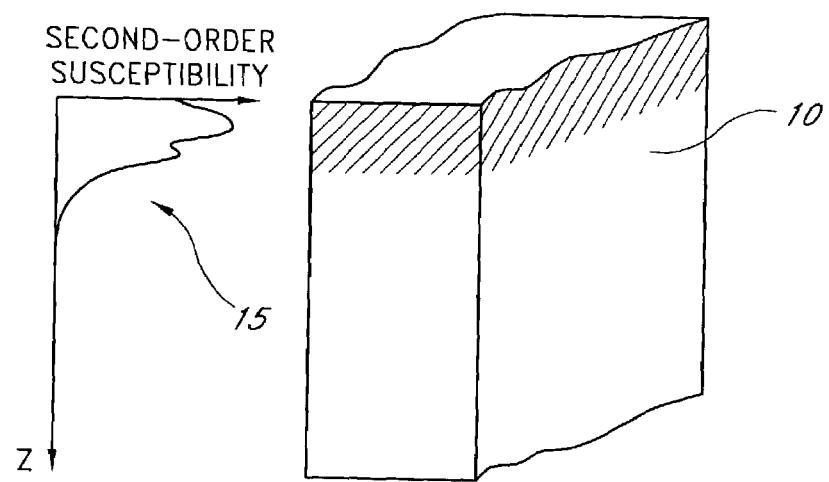
Figure 2:
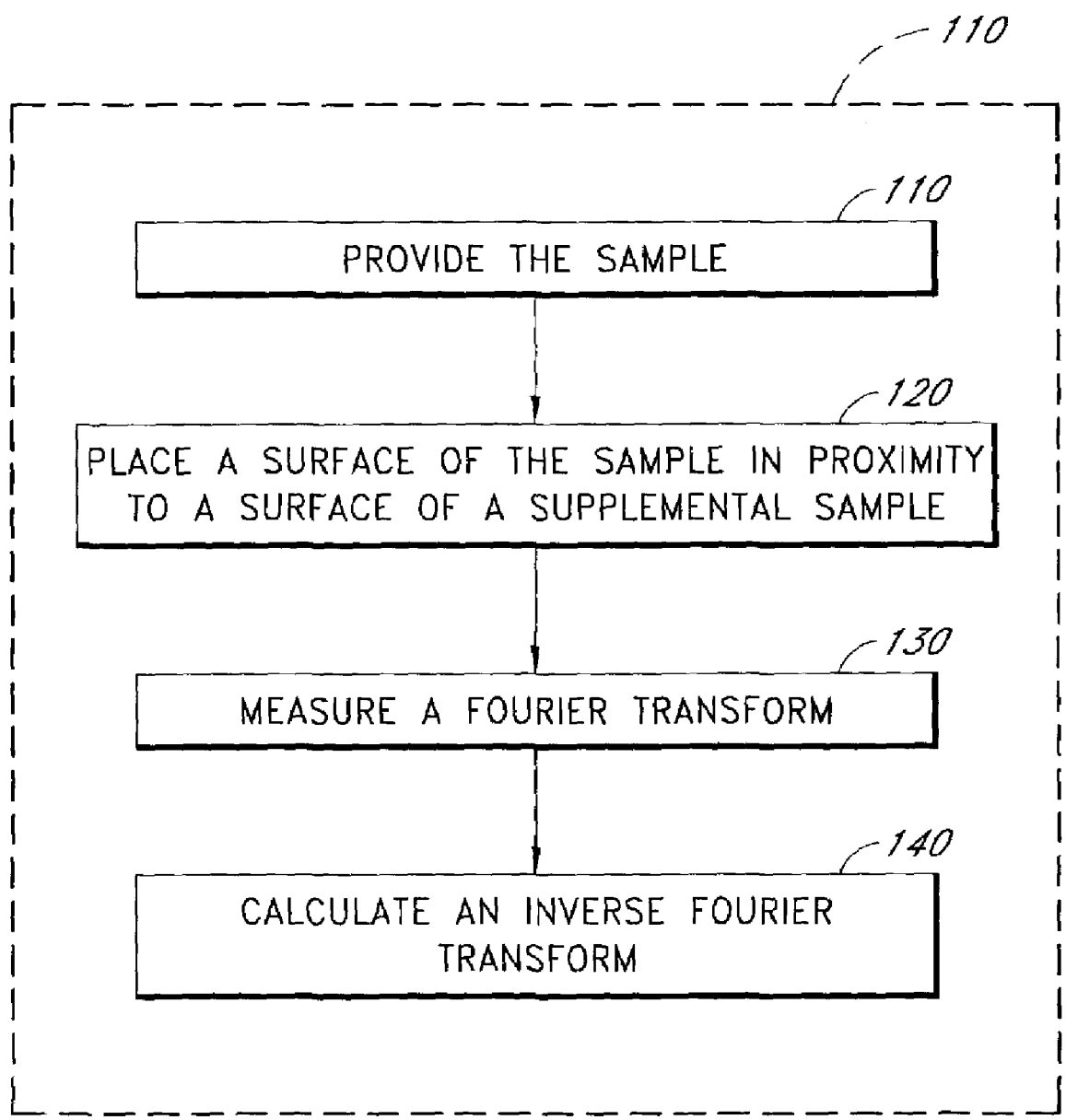
FIG. 2 is a flow diagram of a method of measuring a second-order optical nonlinearity profile of a sample in accordance with embodiments of the present invention.

FIG. 1 is a flow diagram of a method 100 of measuring a second-order optical nonlinearity profile of a sample 10 in accordance with embodiments of the present invention. While the flow diagrams herein illustrate particular embodiments with steps in a particular order, other embodiments with different orders of steps are also compatible with the present invention.

Figure 3A:
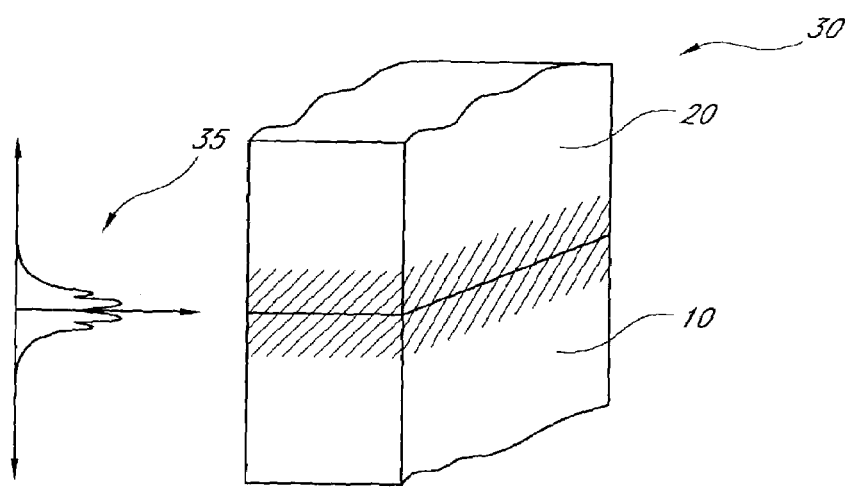
FIG. 3A schematically illustrates a composite sample having a symmetric second-order optical nonlinearity profile.

In the method 100, the sample 10 is provided in an operational block 110. The sample 10 has the second-order optical nonlinearity profile 15 to be measured. In an operational block 120, a surface of the sample 10 is placed in proximity to a surface of a supplemental sample 20, as schematically illustrated in FIGS. 3A–3C and 4A–4D. As schematically illustrated in FIG. 3A, the sample 10 and supplemental sample 20 form a composite sample 30 having a symmetric second-order optical nonlinearity profile 35. In an operational block 130, a Fourier transform of the symmetric second-order optical nonlinearity profile 35 is measured. In an operational block 140, an inverse Fourier transform of the measured Fourier transform is calculated. The calculated inverse Fourier transform provides information regarding the second-order optical nonlinearity profile 15.

In certain embodiments, the information comprises the magnitude and sign of the second-order optical nonlinearity profile 15 as a function of depth below the surface of the sample 10. In other embodiments, information comprises the position of the second-order optical nonlinearity profile 15 below the surface of the sample 10.

In certain embodiments, the second-order optical nonlinearity profile 15 is non-symmetric, while in other embodiments, the second-order optical nonlinearity profile 15 is symmetric. Other existing methods are useful for measuring symmetric second-order optical nonlinearity profiles, but such existing methods are not compatible with non-symmetric profiles. Embodiments described herein are compatible with both symmetric and non-symmetric second-order optical nonlinearity profiles. Since it is not generally known whether the second-order optical nonlinearity profile is symmetric or non-symmetric prior to measurement, embodiments described herein provide a general method of measurement independent of the symmetry of the profile to be determined. In certain embodiments, the information comprises whether the second-order optical nonlinearity profile is symmetric or non-symmetric.

Embodiments of the present invention can be used to determine the nonlinearity profile of any optically nonlinear material (e.g., crystalline, amorphous, organic, or inorganic) in a bulk form or in a film form. In certain embodiments, the nonlinear material comprises an organic material, such as polymers and solids doped with dye molecules. In other embodiments, the nonlinear material comprises inorganic materials such as crystalline lithium niobate or amorphous materials (e.g., oxide-based, fluoride-based, or sulfide-based glasses).

In certain embodiments, the sample 10 comprises silica glass that has been poled so as to induce a second-order optical nonlinearity profile in the sample 10. For example, a fused silica wafer comprised of INFRASIL quartz glass and measuring 1"×1"×0.03" (i.e., 2.54 cm×2.54 cm×7.62 mm) can be poled at approximately 270° C. in air by using an anode electrode placed in proximity to one surface of the wafer and a cathode electrode placed in proximity to the opposite surface of the wafer to apply approximately 5 kV across the wafer for approximately 15 minutes. This procedure results in a second-order optical nonlinearity profile approximately 20–30 μm thick and localized beneath the surface where the anode electrode was placed, as described in more detail by Thomas G. Alley et al. in *Space Charge Dynamics in Thermally Poled Fused Silica*, Journal of Non-Crystalline Solids, Vol. 242, 1998, pages 165–176, which is incorporated herein in its entirety. Other materials and objects (e.g., optical fibers) with inherent or induced second-order optical nonlinearity profiles, and a wide range of poling conditions, are compatible with embodiments of the present invention.

Figure 3B:
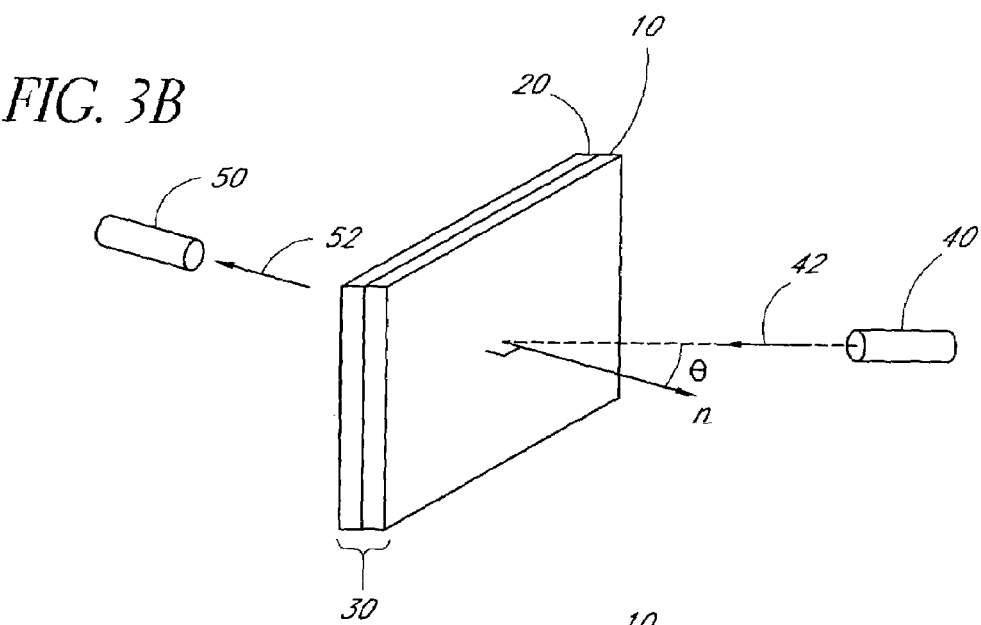
FIGS. 3B and 3C schematically illustrate two measurement configurations in accordance with embodiments of the present invention.
Figure 3C:
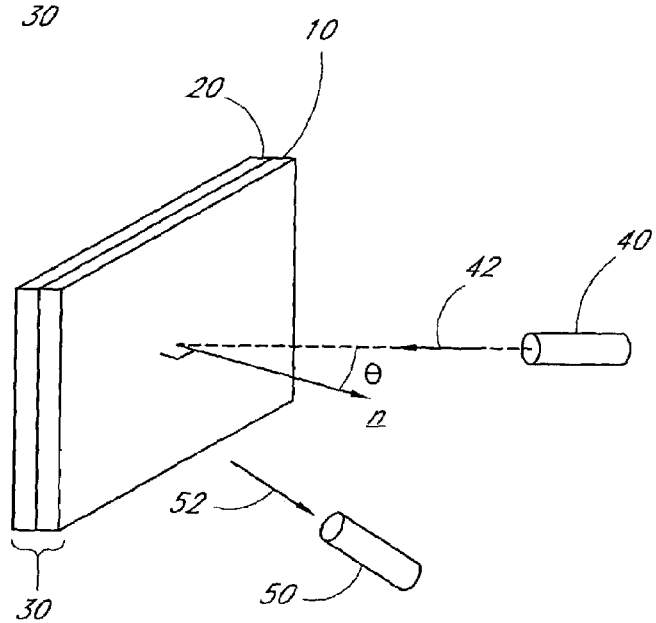

FIGS. 3B and 3C schematically illustrate two measurement configurations in accordance with embodiments of the present invention. In such embodiments, the composite sample 30 has a surface normal direction n. A laser 40 produces a laser beam 42 of light with a fundamental frequency ν. The laser beam 42 is incident on the composite sample 30 at an angle θ relative to the surface normal direction n. In the embodiment of FIG. 3A, a detector 50 is positioned on the opposite side of the composite sample 30 so as to detect the second harmonic (SH) signal 52 (having a frequency 2 ν) from the composite sample 30. In certain embodiments, appropriate optical filters (not shown) are placed between the composite sample 30 and the detector 50 to reduce the laser power transmitted by the composite sample 30 to be well below the weaker power level of the SH signal. The embodiment of FIG. 3B can be considered to be a transmission configuration. In the embodiment of FIG. 3C, the detector 50 is positioned on the same side of the composite sample 30 as the laser 40 so as to detect the SH signal 52. The embodiment of FIG. 3C can be considered to be a reflection configuration.

In certain embodiments, the composite sample 30 is positioned so that the laser beam 42 is first incident on the sample 10, while in other embodiments, the laser beam 42 is first incident on the supplemental sample 20. In certain embodiments, the SH signal 52 is measured as a function of the incident angle θ of the laser beam 42 by rotating the composite sample 30 relative to the laser beam 42.

FIGS. 4A–4D schematically illustrate various embodiments of the supplemental sample 20 in accordance with embodiments of the present invention. In certain embodiments, the supplemental sample 20 has a second-order optical nonlinearity profile substantially identical to that of the sample 10. In the embodiment schematically illustrated in FIG. 4A, the sample 10 and the supplemental sample 20 comprise two portions of a common sample 60. For example, a fused silica wafer which serves as the common sample 60 can be poled as described above, resulting in a poled region 62 beneath the surface 63 of the wafer 60, which is the surface that was placed against the anode electrode during poling. The wafer can then be cut in half, producing two portions 64, 65, which can serve as the sample 10 and the supplemental sample 20. The sample 10 and the supplemental sample 20 can then be sandwiched together, thereby forming the composite sample 30. In certain embodiments, the sample 10 and the supplemental sample 20 are sandwiched together with the poled regions of the portions 64, 65 in proximity to one another (referred to herein as an anode-to-anode configuration). In certain such embodiments, the two halves of the surface 63 are in contact with one another, while in other embodiments, there is empty space or a spacer material between the two portions 64, 65. In other embodiments, the sample 10 and the supplemental sample 20 are sandwiched together with the poled regions of the portions 64, 65 on the outer sides of the composite sample 30 (referred to herein as a cathode-to-cathode configuration). In certain such embodiments, the two portions 64, 65 are in contact with one another, while in other embodiments, there is empty space or a spacer material between the two portions 64, 65.

In the embodiment schematically illustrated in FIG. 4B, the supplemental sample 20 is prepared using substantially identical conditions as those used to prepare the sample 10. For example, two substantially identical fused silica wafers 70, 74 can be poled sequentially or simultaneously as described above using substantially identical conditions, resulting in corresponding poled regions 71, 75 beneath corresponding surfaces 72, 76. In this way, one wafer 70 serves as the sample 10, and the other wafer 74 serves as the supplemental sample 20. The sample 10 and the supplemental sample 20 can then be sandwiched together, thereby forming the composite sample 30. In certain embodiments, the sample 10 and the supplemental sample 20 are sandwiched together with the poled regions 71, 75 in proximity to one another in the anode-to-anode configuration. In certain such embodiments, the two surfaces 72, 76 are in contact with one another, while in other embodiments, there is empty space, or a spacer material, between the two wafers 70, 74. In other embodiments, the sample 10 and the supplemental sample 20 are sandwiched together with the poled regions 71, 75 on opposite sides of the composite sample 30 in the cathode-to-cathode configuration. In certain such embodiments, the two wafers 70, 74 are in contact with one another, while in other embodiments, there is empty space or a spacer material between the two wafers 70, 74.

Figure 4C:
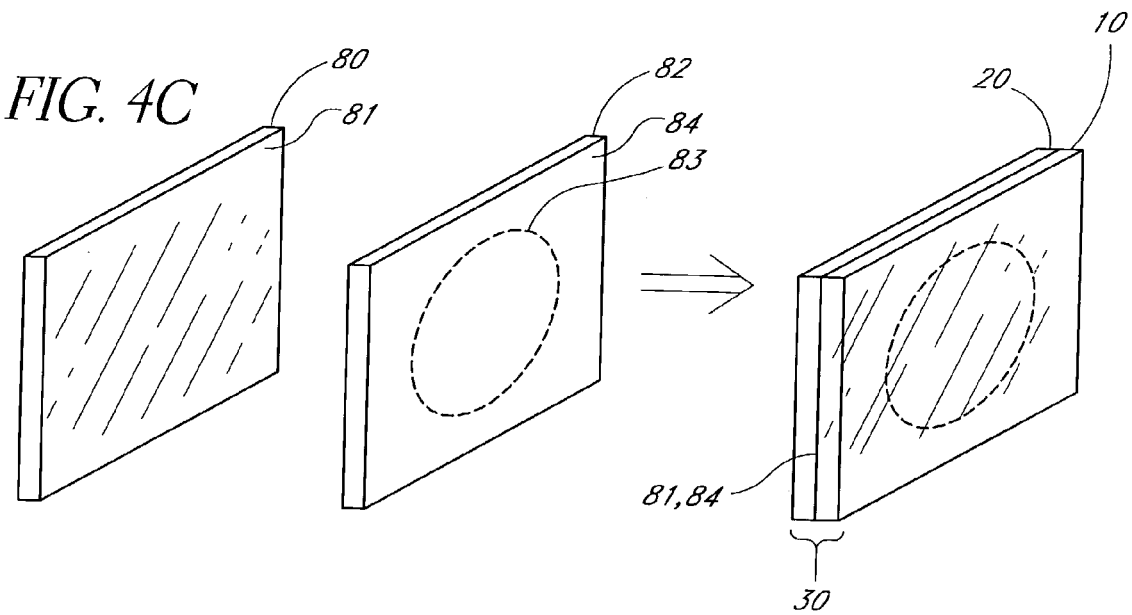

In the embodiment schematically illustrated in FIG. 4C, the supplemental sample 20 comprises a reflector 80 with a reflecting surface 81. The sample 10 of such embodiments can comprise a wafer 82 with a poled region 83 beneath a surface 84 of the wafer 82. The sample 10 and the supplemental sample 20 can then be sandwiched together, thereby forming the composite sample 30. In certain embodiments, the sample 10 and the supplemental sample 20 are sandwiched together with the poled region 83 in proximity to the reflecting surface 81. In certain such embodiments, the reflecting surface 81 and the surface 84 are in contact with one another, while other embodiments have an empty space or a spacer material between the two surfaces 81, 84. When detecting the SH signal 52 in the reflection configuration, the reflector 80 of such embodiments provides an image of the second-order nonlinearity profile of the sample 10 substantially identical to the second-order nonlinearity profile of the sample 10.

Figure 4D:
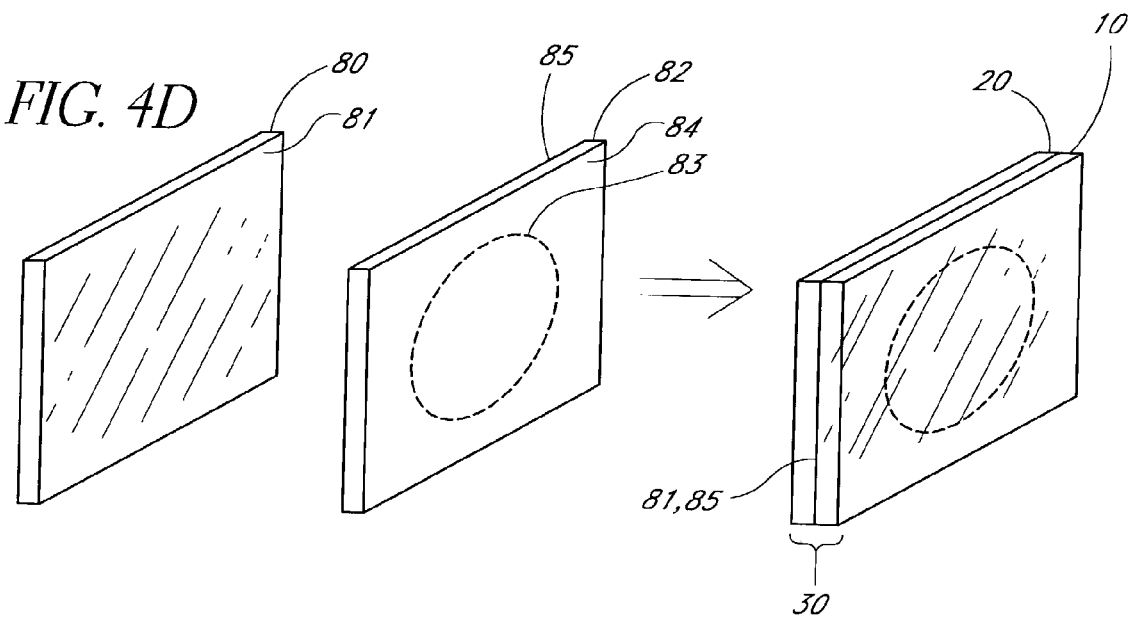

In alternative embodiments, as schematically illustrated in FIG. 4D, the supplemental sample 20 and the poled sample 82 are sandwiched together with the reflecting surface 81 placed against the sample surface 85 on the opposite side of the sample 10 from the surface 84. In certain such embodiments, the two surfaces 81, 85 are in contact with one another, while in other embodiments, there is empty space or a spacer material between the two surfaces 81, 85.

In certain embodiments, placing the sample 10 in proximity to the supplemental sample 20 comprises sandwiching the sample 10 and the supplemental sample 20 together. In certain such embodiments, the sample 10 and the supplemental sample 20 are clamped together, while in other embodiments, the sample 10 and the supplemental sample 20 are glued together. Other methods of placing the sample 10 in proximity to the supplemental sample 20 are compatible with embodiments of the present invention.

Figure 5:
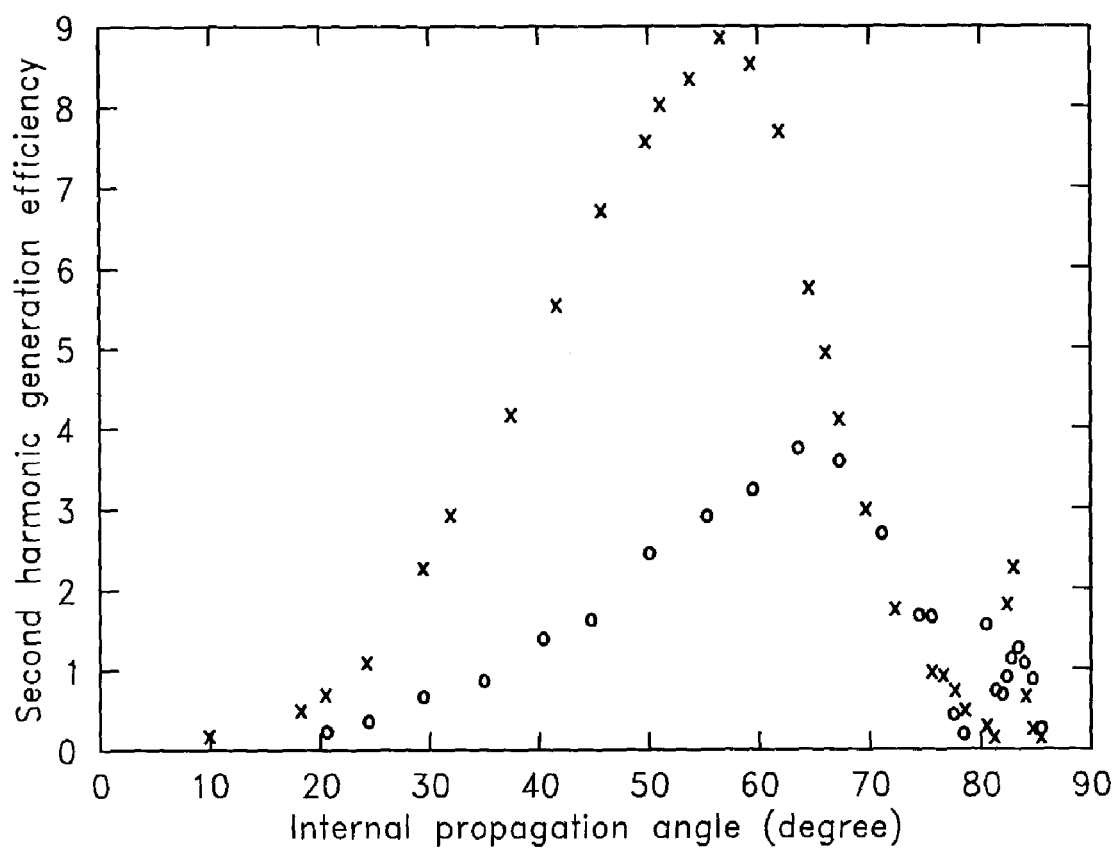
FIG. 5 illustrates exemplary Maker fringe profiles (in units of $10^{-19}$ m$^2$/W) measured from a common sample (shown as open circles) and a composite sample (shown as crosses).

FIG. 5 illustrates exemplary Maker fringe profiles measured from a common sample 60 (shown as open circles) and from a composite sample 30 (shown as crosses). As described above, the measured fringe profile corresponds to the Fourier transform of the second-order optical nonlinearity profile. In certain embodiments, measuring the Fourier transform comprises measuring the Maker fringe profile of the composite sample 30. The composite sample 30 was formed by cutting the common sample 60 in half and placing the two halves in proximity to one another with the surfaces near the poled regions in contact with one another. The fringe profile of the composite sample 30 is more intense and is shifted towards lower angles than that of the common sample 60 because the nonlinear region of the composite sample 30 is twice as thick as the nonlinear region of the common sample 60.

Figure 6A:
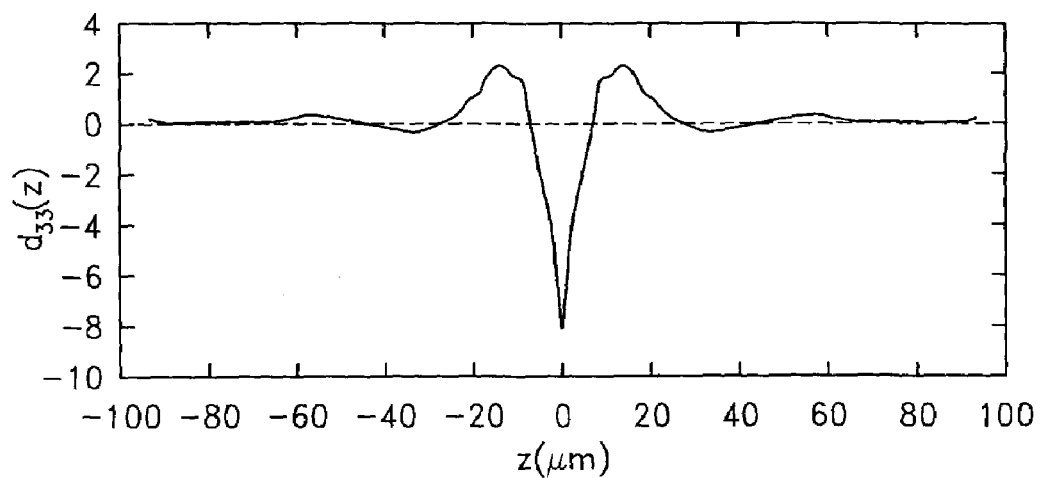
FIG. 6A illustrates the second-order nonlinearity profile $d_{33}(z)$ (in units of $10^{-13}$ m/V) of the composite sample obtained by calculating the inverse Fourier transform of the measured fringe profile from the composite sample as illustrated in FIG. 5.
Figure 6B:
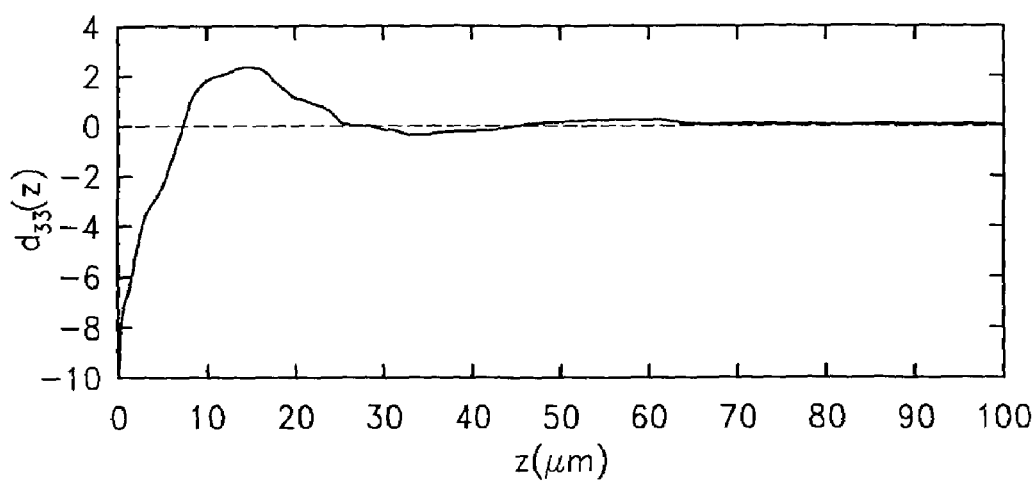
FIG. 6B illustrates the original nonlinearity profile $d_{33}(z)$ (in units of $10^{-13}$ m/V) of the sample corresponding to the z>0 portion of the nonlinearity profile of FIG. 6A.

FIG. 6A illustrates the second-order nonlinearity profile $d_{33}(z)$ of the composite sample 30 obtained by calculating the inverse Fourier transform of the measured fringe profile from the composite sample 30 as illustrated in FIG. 5. The abscissa z=0 corresponds to the boundary between the mated surfaces of the sandwiched sample 10 and the supplemental sample 20. By construction, the nonlinearity profile of the composite sample 30 is the juxtaposition of the $d_{33}(z)$ profile of the sample 10 and its mirror image $d_{33}(-z)$ from the supplemental sample 20. By retaining only the z>0 portion of the nonlinearity profile of FIG. 6A, the original nonlinearity profile $d_{33}(z)$ of the sample 10 is directly obtained, as illustrated in FIG. 6B. The nonlinearity profile of FIG. 6B represents an unambiguously derived nonlinearity profile of the thermally poled silica sample 10. The need for the phase information has been eliminated by artificially creating a symmetric nonlinearity profile based on the nonlinearity profile of the sample 10.

FIG. 6B also includes information regarding the depth location of the nonlinearity, which would not be available using prior methods, even if the phase information was retrieved. FIG. 6B shows that $d_{33}(z)$ changes sign three times and that its peak value is −0.8 picometer per volt (pm/V). This result is the highest reliable value of $d_{33}(z)$ reported for thermally poled silica. The peak of the nonlinearity profile is located just under the surface, and the poled region extends approximately 25 µm under the surface.

The main mechanism believed to be responsible for the second-order optical susceptibility $\chi^{(2)}$ in thermally poled silica is DC rectification of the third-order optical susceptibility $\chi^{(3)}$ of silica. As described more fully by D. Faccio et al. and T. G. Alley et al. (cited above), the second-order susceptibility $\chi^{(2)}$ is proportional to $\chi^{(3)}E(z)$, where $E(z)$ is the permanent electric field that develops inside the glass during poling.

Figure 7:
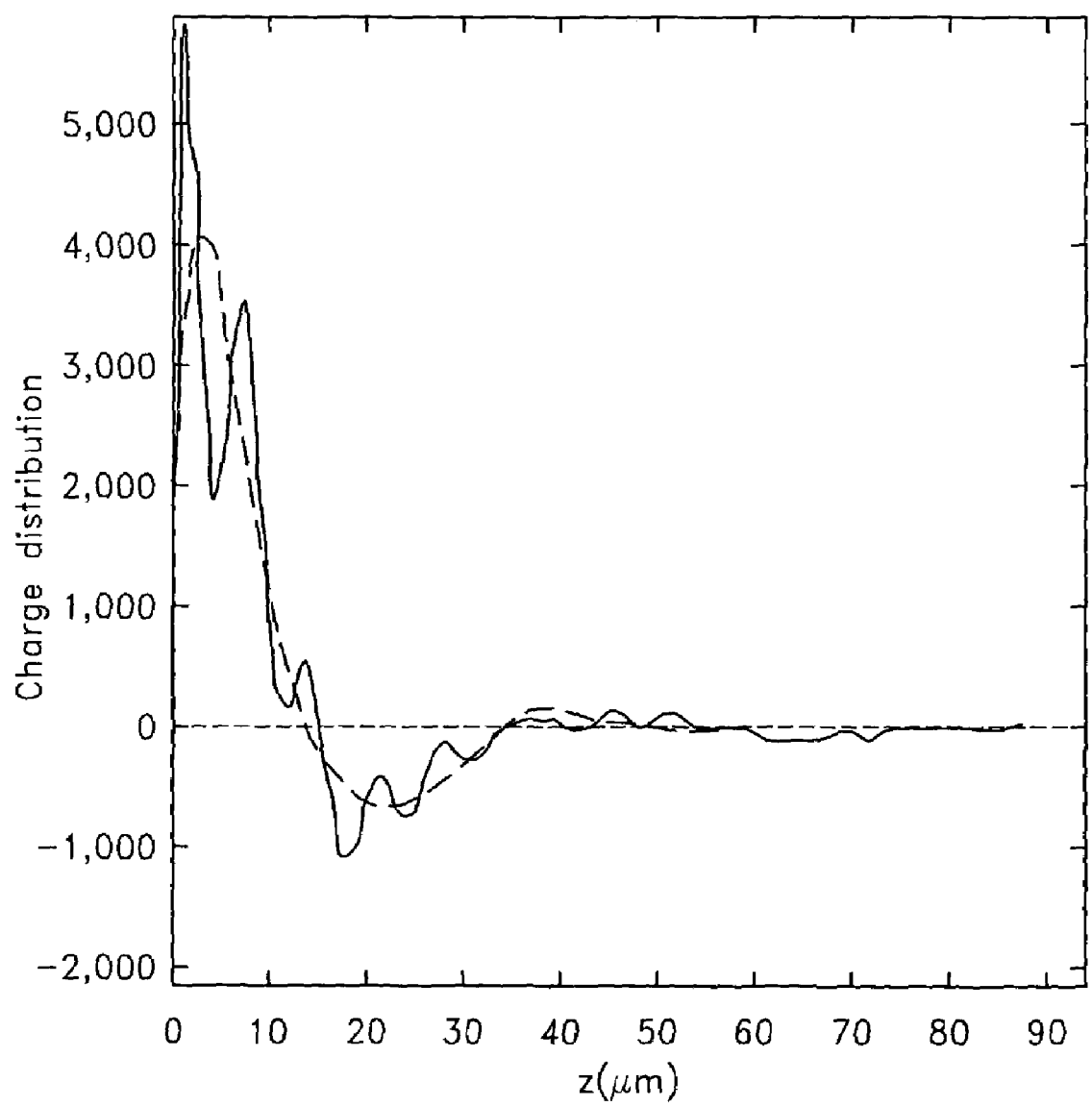
FIG. 7 illustrates the charge distribution $\rho(z)$ (in units of C/m$^3$) derived from the nonlinearity profile of FIG. 6B.

The charge distribution within the glass which generates the permanent electric field $E(z)$ can be determined from the nonlinearity profile $d_{33}(z)$. Since the poled region is essentially a thin infinite plane, the electric field $E(z)$ is related to the charge density $\rho(z)$ by the one-dimensional form of Maxwell's equation, $\delta E/\delta z = \rho(z)/\in$, where $\in$ is the dielectric susceptibility of the medium. Since $d_{33}(z)$ is proportional to $E(z)$, the charge distribution $\rho(z)$ can be derived by differentiating the profile $d_{33}(z)$. Applied to the nonlinearity profile of FIG. 6B, this method yields the charge distribution of FIG. 7. The solid curve of FIG. 7 is derived directly from the Maker fringe data by taking the derivative of the $d_{33}(z)$ profile of FIG. 6B. The oscillatory behavior is a numerical artifact resulting from the finite angular sampling of the measured Maker fringe data of FIG. 5. The dashed curve is a best-fit polynomial function to the solid curve.

The charge distribution $\rho(z)$ shows an accumulation of positive charge near the surface, with a negatively charged region deeper in the sample 10. The centers of the two regions are separated by approximately 15 µm. A smaller, positively charged region is also apparent approximately 45 µm into the sample 10. The charge distribution illustrated by FIG. 7 agrees qualitatively with results obtained with alternative techniques. Examples of these alternative techniques are described by P. G. Kazansky et al. in *Thermally Poled Silica Glass: Laser Induced Pressure Pulse Probe of Charge Distribution*, Applied Physics Letters, Vol. 68, 1996, pages 269–271, which is incorporated in its entirety by reference herein, and by D. Faccio et al. (cited above).

Figure 8:
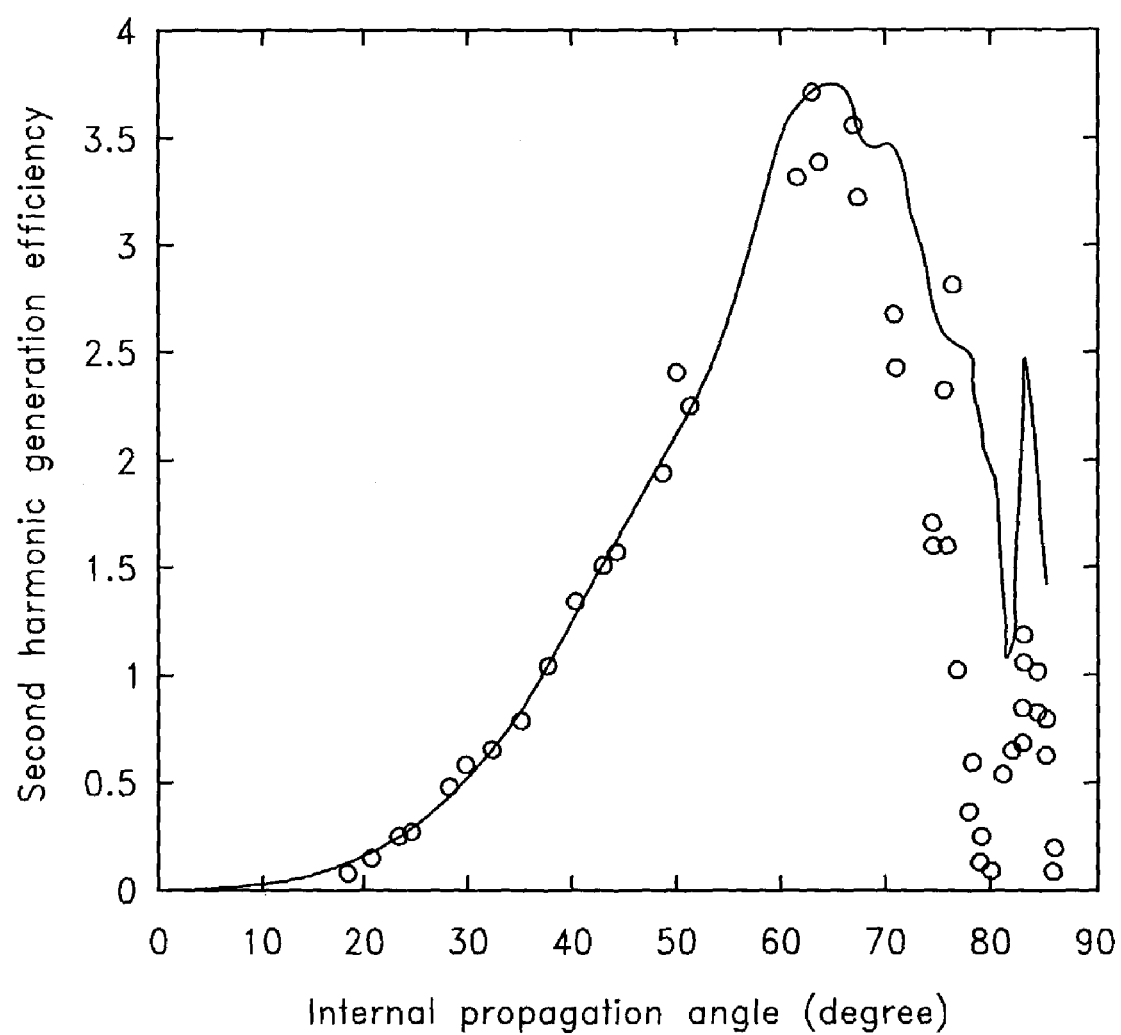
FIG. 8 illustrates the comparison of the measured fringe profile (in units of $10^{-19}$ m$^2$/W) from the original sample (open circles) with a theoretical fringe profile calculated from $d_{33}(z)$ (as shown in FIG. 6B) obtained from the measured SH signal from the composite sample (solid line).

The nonlinearity profile derived in accordance with embodiments of the present invention can be independently verified by comparing the measured Maker fringe profile from the original sample 10 (shown as open circles in FIG. 5 and FIG. 8) with the theoretical fringe profile (solid curve in FIG. 8) calculated from $d_{33}(z)$ obtained from the measured SH signal from the composite sample 30 (FIG. 6B). This comparison, illustrated in FIG. 8, shows that the two fringe profiles agree reasonably well, and that in particular, the spatial uniformity of the second-order susceptibility of the sample 10 was sufficient to infer the nonlinearity profile reliably.

Embodiments of the present invention enable the second-order nonlinearity profile of an optically nonlinear film to be inferred unambiguously from a Maker fringe profile measurement. As described above, the nonlinearity profile of an exemplary thermally poled silica sample has been determined to: (i) have a peak value of approximately −0.8 µm/V, (ii) extend approximately 25 µm below the sample surface, and (iii) take both positive and negative values. Such magnitude and spatial information of the nonlinearity profile and of the charge distribution has significant implications in the design of future devices based on thermally poled silica.

Figure 9:
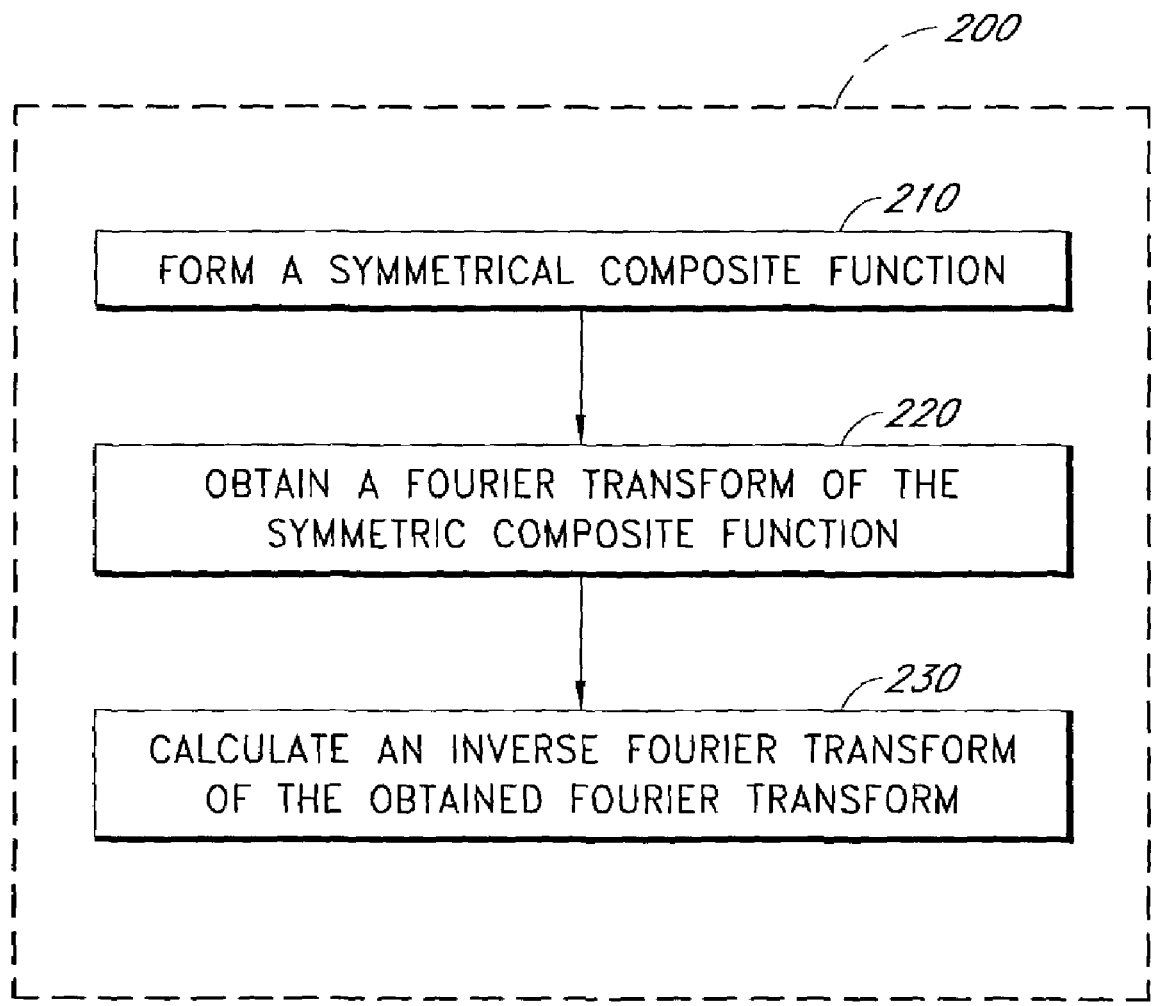
FIG. 9 is a flowchart of a method in accordance with embodiments of the present invention for measuring physical functions.

Embodiments of the method can be used to measure other physical functions. FIG. 9 is a flowchart of a method 200 in accordance with embodiments of the present invention. In an operational block 210, a symmetric composite function is formed by superimposing the physical function with a substantially identical physical function. In an operational block 220, a Fourier transform of the symmetric composite function is obtained. In an operational block 230, an inverse Fourier transform of the obtained Fourier transform is calculated. The calculated inverse Fourier transform provides information regarding the physical function.

For example, instead of forming a symmetric composite function in the spatial domain as described above in relation to the nonlinearity profile of poled silica, other embodiments form a symmetric intensity profile in the time domain by the use of time reversal. In such embodiments, the symmetric composite function can have utility where phase information is needed but unavailable (e.g., ultra-short pulse diagnosis using auto-correlators). An example of time reversal is described by D. A. B. Miller in *Time Reversal of Optical Pulses by Four-Wave Mixing*, Optics Letters Vol. 5, 1980, pages 300–302, which is incorporated in its entirety by reference herein.

Figure 10:
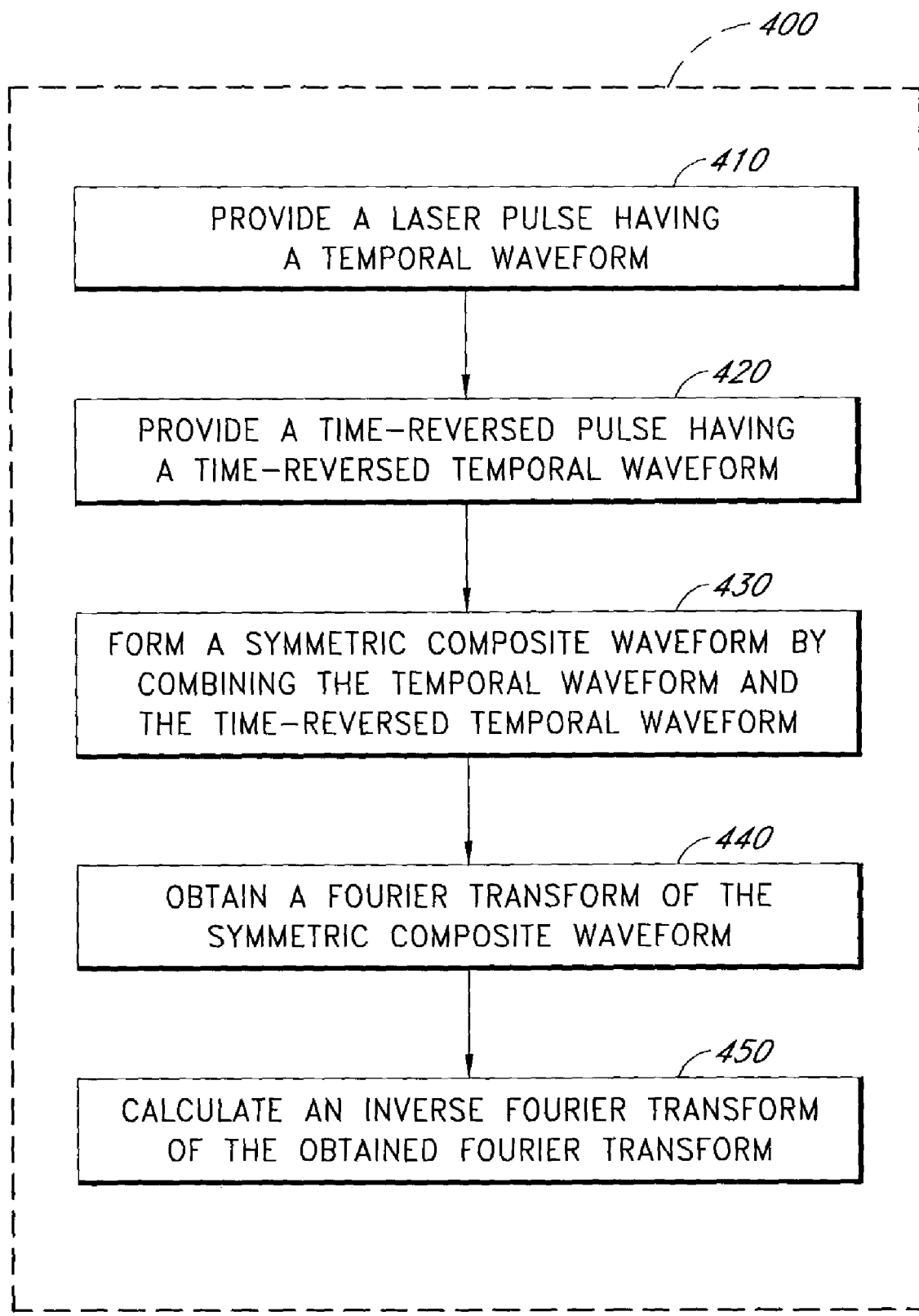
FIG. 10 is a flow diagram of a method of determining the temporal waveform of a laser pulse in accordance with embodiments of the present invention.
Figure 11:
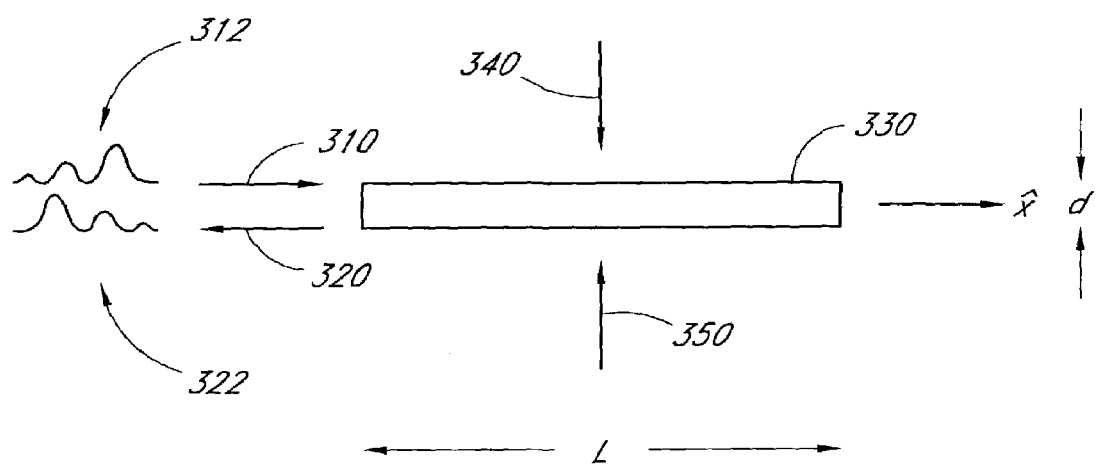
FIG. 11 schematically illustrates four-wave mixing (FWM) with pulsed pumps for providing the time-reversed pulse in accordance with embodiments of the present invention.

FIG. 10 is a flow diagram of a method 400 of determining the temporal waveform 312 of a laser pulse 310 in accordance with embodiments of the present invention. FIG. 11 schematically illustrates one configuration for utilizing four-wave mixing (FWM) to provide the time-reversed pulse 320 in accordance with embodiments of the present invention. Other configurations are also compatible with the method of FIG. 10. Referring to the elements illustrated in FIG. 11, in an operational block 410, a laser pulse 310 is provided. The laser pulse 310 has a temporal waveform 312. In an operational block 420, a time-reversed pulse 320 is provided. The time-reversed pulse 320 has a time-reversed temporal waveform 322 which corresponds to the temporal waveform 312 after being time-reversed. In an operational block 430, the temporal waveform 312 of the laser pulse 310 and the time-reversed temporal waveform 322 of the time-reversed pulse 320 form a symmetric composite waveform. In an operational block 440, a Fourier transform of the symmetric composite waveform is obtained. In an operational block 450, an inverse Fourier transform of the obtained Fourier transform is calculated. The calculated inverse Fourier transform provides information regarding the temporal waveform 312 of the laser pulse 310.

FWM has been a subject of interest in applications such as aberration compensation, spatial information processing, frequency filtering, pulse envelope shaping, and dispersion compensation. As illustrated in FIG. 11, a nonlinear medium 330 of length L is pumped by two pulsed pump waves 340, 350. An input laser pulse 310 (with temporal waveform 312 given by $E_p(x,t)$) launched into the nonlinear medium 330 generates a phase conjugate pulse 320 (with time-reversed temporal waveform 322 given by $E_c(x,t)$), which is the time-reversed version of the temporal waveform 312 of the input pulse 310. In the embodiment described below, the input pulse 310, two pump waves 340, 350, and the nonlinear medium are at the same place for the duration of the input pulse 310. In addition, the input pulse 310, and the two pump waves 340, 350 overlap in the frequency domain.

Illustratively, the temporal waveform 312 of the input pulse 310 can be written in the following form:

$$E_p(x,t) = \frac{1}{2} u_p(t) e^{j(\omega_p t - kx)} + \text{complex conjugate.} \quad (2)$$

where $u_p(t)$ is the modulation of the carrier $e^{j(\omega_p t - kx)}$. The Fourier transform of $u_p(t)$ has the following form:

$$\overline{U}_p(\omega) = \int u_p(t) e^{-j\omega t} dt. \quad (3)$$

The temporal waveform of the resultant conjugate pulse 320 has the following form:

$$E_c(x,t) = \frac{1}{2} u_c(t) e^{j(\omega_c t + kx)} + \text{complex conjugate.} \quad (4)$$

where "c" stands for "conjugate." Note that the k-vector of the conjugate pulse $E_c(x,t)$ has the reverse sign as expected. The Fourier transform of the envelope function $u_c(t)$ is defined the same way:

$$i\ \overline{U}_c(\omega) = \int u_c(t) e^{-j\omega t} dt. \quad (5)$$

The relationship between the carrier frequencies $\omega_c$, $\omega_p$, as defined above, and the center frequencies $\omega_{pump,1}$ and $\omega_{pump,2}$ of the two pumps 340, 350 is:

$$\omega_{pump,1} + \omega_{pump,2} - \omega_p = \omega_c \quad (6)$$

With these definitions, the envelope function $u_c(t)$ can be expressed as:

$$u_c(t) = \int h(\omega) \overline{U}_p^*(-\omega) e^{j\omega t} d\omega \quad (7)$$

where $h(\omega)$ is the response function of the nonlinear material 330. For broadband conjugators (with respect to the spectrum of $u_p(t)$), $h(\omega)$ can be taken as a constant (K), giving $u_c(t)$ the following form:

$$u_c(t) = K \int \overline{U}_p^*(-\omega) e^{j\omega t} d\omega. \quad (8)$$

The foregoing forms of the envelope function $u_c(t)$ were obtained using the teachings of R. A. Fischer et al. in *Transient Analysis of Kerr-Like Phase Conjugators Using Frequency-Domain Techniques*, Physical Review A, Vol. 23, 1981, pages 3071–3083, which is incorporated in its entirety by reference herein.

The above equations can be used to show that for continuous-wave (CW) pumping, FWM can not time-reverse pulsed fields. This property of FWM in CW pumping has been extensively studied for dispersion compensation in fiber links. Examples of such work include A. Yariv et al. in *Compensation for Channel Dispersion by Nonlinear Optical Phase Conjugation*, Optics Letters Vol. 4, 1979, pages 52–54, and S. Watanabe et al. in *Compensation of Chromatic Dispersion in a Single-Mode Fiber by Optical Phase Conjugation*, IEEE Photonics Technical Letters, Vol. 5, 1993, pages 92–95, both of which are incorporated in their entirety by reference herein.

However, pulsed pumping can be used to achieve time reversal of amplitude pulses. Following the derivation of D. A. B. Miller (cited above), $u_c(t)$ can be expressed as:

$$u_c(t) = K' u_p^*(-t + \tau_0) \quad (9)$$

where K' and $\tau_0$ are constants. The −t term in Equation 9 indicates the time reversal operation. Note that Equation 2 and Equation 6 are still valid for this case. The assumptions made in the derivation of Equation 9 are that:

(1) the nonlinear medium 330 has a length L equal to or longer than the spatial length of the input pulse 310 (i.e., large L assumption) so that the input pulse 310 is completely within the nonlinear medium 330 at some time during the interaction;

(2) the pump pulses 340, 350 are perpendicular to the nonlinear medium as shown in FIG. 11;

(3) pump pulses 340, 350 are short compared with the input pulse 310 (i.e., the spectra of both pump pulses 340, 350 are broad enough so that all of the frequency components of the input pulse 310 see a substantially uniform pump spectral power density for both pumps);

(4) as a consequence of (3), the thickness of the nonlinear medium 330 is preferably equal to or slightly greater than the spatial length of the pump pulses 340, 350); and (5) the timing of the pulses is such that when pulse 310 spatially fills the nonlinear medium 330 (i.e. the input pulse 310 is fully within the medium), the pump pulses 340 and 350 are timed to be overlapping in space with the input pulse 310 across the nonlinear medium filled by the input pulse.

Some of the details of these assumptions can be found in D. A. B. Miller's work (cited above). As described below, the apparatus schematically illustrated by FIG. 11 can serve as a phase conjugate mirror which generates the time-reversed waveform corresponding to an input waveform.

In other embodiments, the time-reversed pulse 320 can be provided using holographic techniques in accordance with embodiments of the present invention. Femtosecond spectral holography can be considered as a temporal analog of the classical spatial domain holography. In classical holography, a spatial information carrying beam (signal) and a uniform reference beam interfere in a recording medium, thereby recording a hologram comprising a set of fringes. Illumination of the hologram with a uniform test beam reconstructs either a real or conjugate image of the signal beam, depending on the geometry.

Figure 12A:
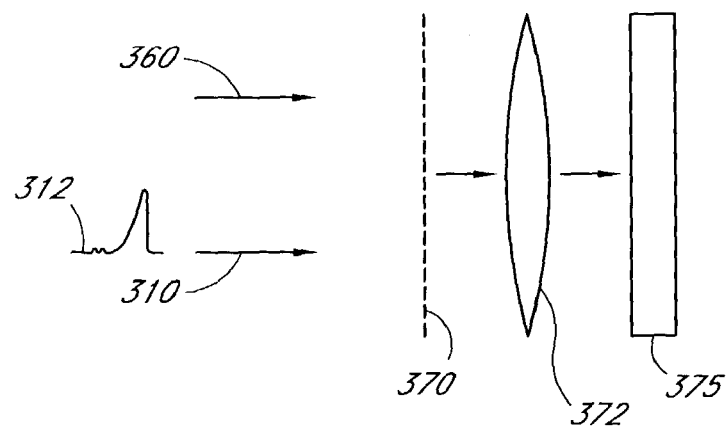
FIGS. 12A and 12B schematically illustrate femtosecond spectral holography for providing the time-reversed pulse in accordance with embodiments of the present invention.
Figure 12B:
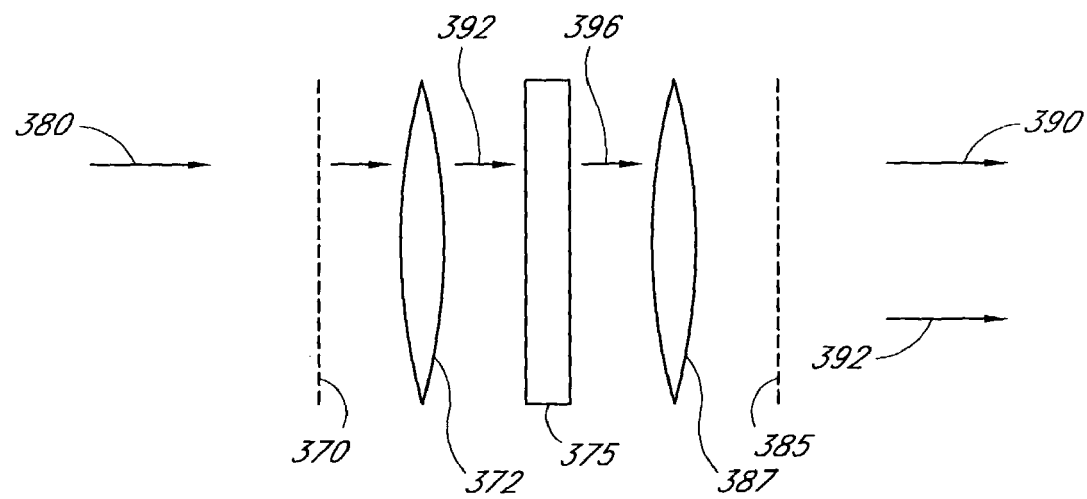

Femtosecond spectral holography for the time reversal process comprises a recording phase and a read-out phase, as schematically illustrated respectively by FIGS. 12A and 12B. In the recording phase (FIG. 12A), the reference pulse 360 is short with a relatively flat and broad spectrum, and the input pulse 310 has a temporal waveform 312 that has a shape indicative of information carried by the input pulse 310. During the recording of the hologram, a grating 370 is used to disperse both the reference pulse 360 and the input pulse 310 into their spectral components, which then propagate through a collimating lens system 372. The interference pattern formed by the complex amplitudes of each spectral component is then recorded in the holographic recording plate 375.

In the read-out phase (FIG. 12B), a short test pulse 380 is dispersed by the grating 370 and then recollimated by the lens 372. The illumination of the holographic plate 375 with this recollimated dispersed test beam 392 produces the beam 396. Using the lens 387 for recollimation and the second grating 385, a time-reversed replica 390 of the original input pulse 310 is produced. Also as a by-product, the transmitted test beam 392 appears at the output. The details of this technique are described more fully by A. M. Weiner et al. in *Femtosecond Spectral Holography*, IEEE Journal of Quantum Electronics, Vol. 28, 1992, pages 2251–2261, and A. M. Weiner et al. in *Femtosecond Pulse Shaping for Synthesis,*

*Processing and Time-to-Space Conversion of Ultrafast Optical Waveforms*, IEEE Journal of Selected Topics in Quantum Electronics, Vol. 4, 1998, pages 317–331, both of which are incorporated in their entireties by reference herein.

The envelope of the output pulse 390 can be expressed as:

$$u_{out}(t) \approx u_t(t) * u_r(-t) * u_s(t) e^{j\overline{K}_1 \vec{r}} + u_t(t) * u_r(t) * u_s(-t) e^{j\overline{K}_2 \vec{r}} \quad (10)$$

where $u_{out}(t)$, $u_t(t)$, $u_r(t)$, and $u_s(t)$ are the complex envelope functions of the electric fields of the output pulse 390, test pulse 380, reference pulse 360, and input pulse 310, respectively. The sign '*' denotes the convolution function, and $\overline{K}_1 = \overline{k}_t - \overline{k}_r + \overline{k}_s$ and $\overline{K}_2 = \overline{k}_t + \overline{k}_r - \overline{k}_s$.

When the test pulse 380 and the reference pulse 360 are considerably shorter than the input pulse 310, $u_s(t)$, $u_t(t)$, and $u_r(t)$ will act as delta functions with respect to $u_s(t)$, modifying the envelope of the output pulse 390 to be:

$$u_{out}(t) \approx u_s(t) e^{j\overline{K}_1 \vec{r}} + u_s(-t) e^{j\overline{K}_2 \vec{r}}. \quad (11)$$

Therefore, as a result of the illumination of the holographic plate with the test pulse 380, the output pulse 390 serves as the time-reversed signal pulse 320 in the $\overline{K}_2$ direction. As described below, the apparatus schematically illustrated by FIGS. 12A and 12B can serve as a phase conjugate mirror which generates the time-reversed waveform corresponding to an input waveform.

Note that embodiments of both the pulse-pumped FWM and the spectral holography techniques use shorter pulses than the input pulse 310 to time-reverse the input pulse 310. For pulse-pumped FWM, shorter pump pulses 340, 350 are used, and for holography, shorter test pulses 380 and reference pulses 360 are used.

Figure 13:
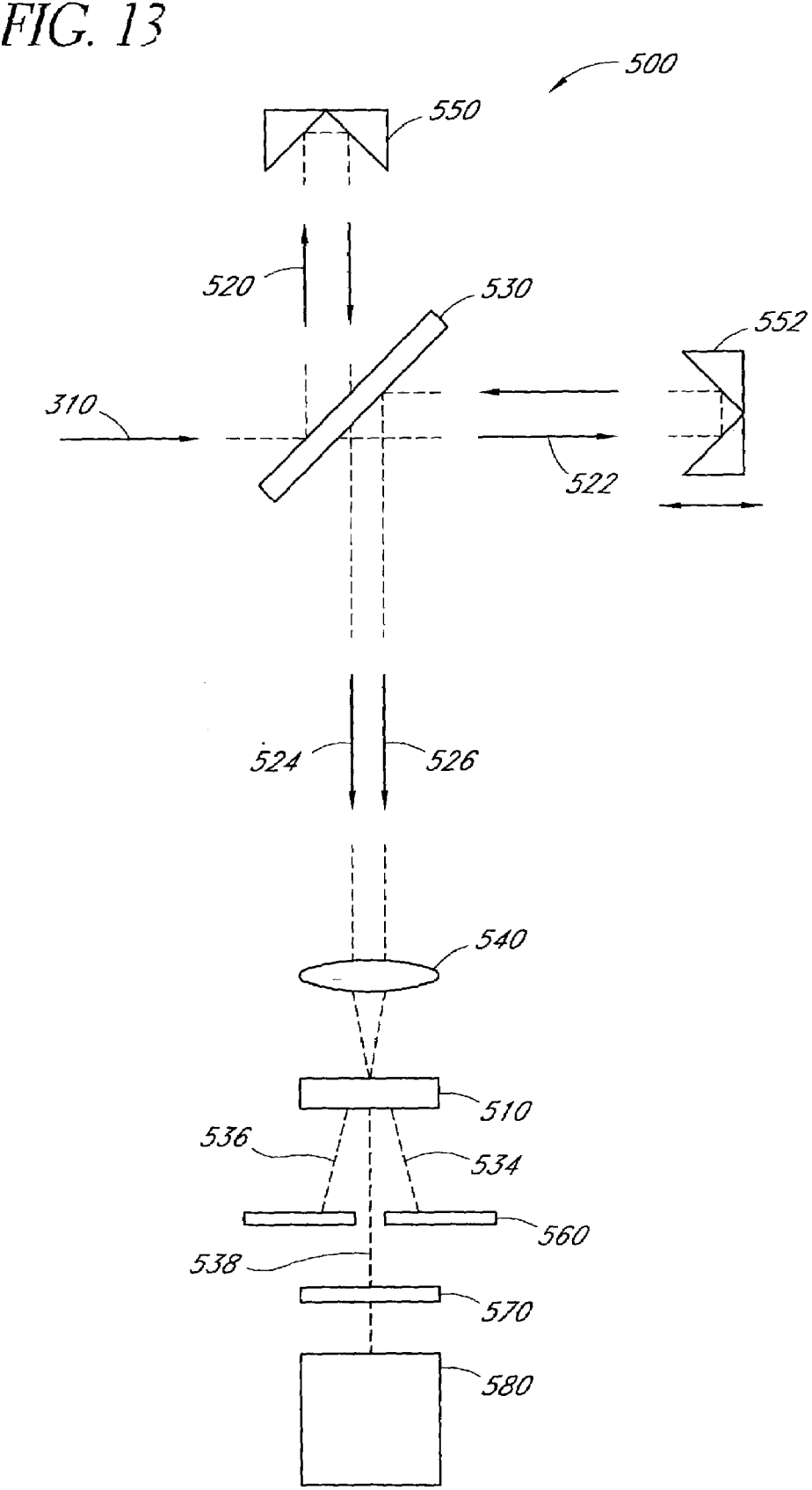
FIG. 13 schematically illustrates one embodiment of a classical intensity correlator utilizing a Michelson interferometer.

In certain embodiments for estimating the temporal waveform of a laser pulse, a classical correlator configuration is used with a second-harmonic generating (SHG) crystal 510. FIG. 13 schematically illustrates one embodiment of a classical intensity correlator utilizing a Michelson interferometer 500. The input pulse 310 is split into a first pulse 520 and a second pulse 522 by the beamsplitter 530. The first pulse 520 is reflected by a fixed mirror 550 back through the beamsplitter 530, thereby transmitting a third pulse 524. The second pulse 522 is reflected by a movable mirror 552 back through the beamsplitter 530, thereby transmitting a fourth pulse 526 towards the focusing lens 540. The movable mirror 552 adds a variable delay r to the fourth pulse 526 with respect to the third pulse 524. The focusing lens 540 focuses the third pulse 524 and the fourth pulse 526 onto the SHG crystal 510. The SHG crystal 510 generates a second-harmonic (SH) field 538 which is a cross-correlation product of the third pulse 524 and the fourth pulse 526. Other SH fields 534, 536 generated by the SHG crystal 510 do not carry information regarding the third and fourth pulses 524, 526 simultaneously, and these other SH fields are blocked by the pinhole 560 placed after the SHG crystal 510. After passing through a filter 570 which blocks light at the fundamental wavelength and which passes the SH light, the cross-correlation product 538 is detected by a photomultiplier tube 580.

The third pulse 524 emerging from one arm of the Michelson interferometer 500 has a waveform given by:

$$E_1(t) = u_1(t) e^{j\omega t} \quad (12)$$

where $u_1(t)$ is the complex envelope function of the input pulse 310. The fourth pulse 526 emerging from the other arm of the Michelson interferometer 500 has a waveform given by:

$$E_2(t) = u_2(t) e^{j\omega t} = u_1(t-\tau) e^{j\omega(t-\tau)} \quad (13)$$

where $\tau$ is the relative time delay between the third pulse 524 and the fourth pulse 526 imposed by the delay $\tau$ between the two arms. Because of the focusing lens 540, the third pulse 524 and the fourth pulse 526 have different k-vectors at the surface of the SHG crystal 510. Consequently, the SH field 538 generated by the SHG crystal 510 that is not blocked by the pinhole 560 includes only terms due to the interaction of the third pulse 524 and the fourth pulse 526, and has a waveform given by:

$$E_{2\omega}(t) = u_{2\omega}(t) e^{j2\omega t} = \eta u_1(t) u_2(t) e^{j2\omega t} = \eta u_1(t) u_1(t-\tau) e^{-j\omega\tau} e^{j2\omega t}. \quad (14)$$

where $\eta$ is a conversion efficiency factor corresponding to the SHG crystal and the system geometry. The signal detected by the photomultiplier 580 (i.e., the autocorrelation function) is given by:

$$A_{PMT}(\tau) = \int E_{2\omega}(t) E^*_{2\omega}(t) dt = \int |\eta|^2 |u_1(t)|^2 |u_1(t-\tau)|^2 dt = |\eta|^2 \int I(t) I(t-\tau) dt \quad (15)$$

where $I(t) = |u_1(t)|^2$ is the input signal intensity. In general, $\eta$ is a function of frequency and the functions $u_1(t)$ and $u_2(t)$ can be expanded as plane waves with Fourier transform amplitudes (i.e., $u_i(t) = \int U_i(\omega) e^{j\omega t} d\omega$). However, it is assumed here that $\eta$ is constant over the frequency range of the combined pulses, which is equivalent to assuming that $\chi^{(2)}$ is independent of frequency. This assumption holds when the effective crystal length is shorter than the coherence length of the harmonic generation over the pulse bandwidth.

By taking the Fourier transform of both sides of Equation 15 (the signal detected by the photomultiplier 580 for a single pulse) provides the Fourier transform of the autocorrelation function and is given by:

$$\overline{A}_{PMT\_single}(f) = |\eta|^2 |\overline{I}(f)|^2 \quad (16)$$

where $\overline{A}_{PMT\_single}(f)$ and $\overline{I}(f)$ are the Fourier transforms of $A_{PMT}(\tau)$ and $I(\tau)$, respectively. Thus, the signal from the Michelson interferometer 500 of FIG. 12 provides the magnitude of the Fourier transform of the input pulse intensity $I(t)$.

However, the magnitude of the Fourier transform is not sufficient information to retrieve uniquely the input pulse intensity $I(t)$. To do so would also require the knowledge of the phase of the Fourier transform, which this classical autocorrelation method does not provide. This difficulty in uniquely determining the input pulse intensity $I(t)$ is analogous to that of retrieving the second-order susceptibility spatial profile of a nonlinear material, as described above. In practice, a number of methods can be used to avoid this difficulty. For example, a certain shape for the pulse intensity (e.g., a Gaussian) can be assumed, but there is no way to independently verify that the assumed shape is the true temporal waveform. This method therefore provides only an estimate of the pulse shape.

By using a time-reversal technique compatible with embodiments of the present invention (e.g., pulse-pumped FWM or femtosecond spectral holography), a time-reversed pulse with a time-reversed temporal waveform $I(-t)$ of the temporal waveform $I(t)$ of an arbitrary pulse can be produced. A symmetric composite waveform can then be formed by delaying the time-reversed pulse with respect to the original pulse and combining the temporal waveform with the time-reversed temporal waveform, for example with a beamsplitter.

Figure 14:
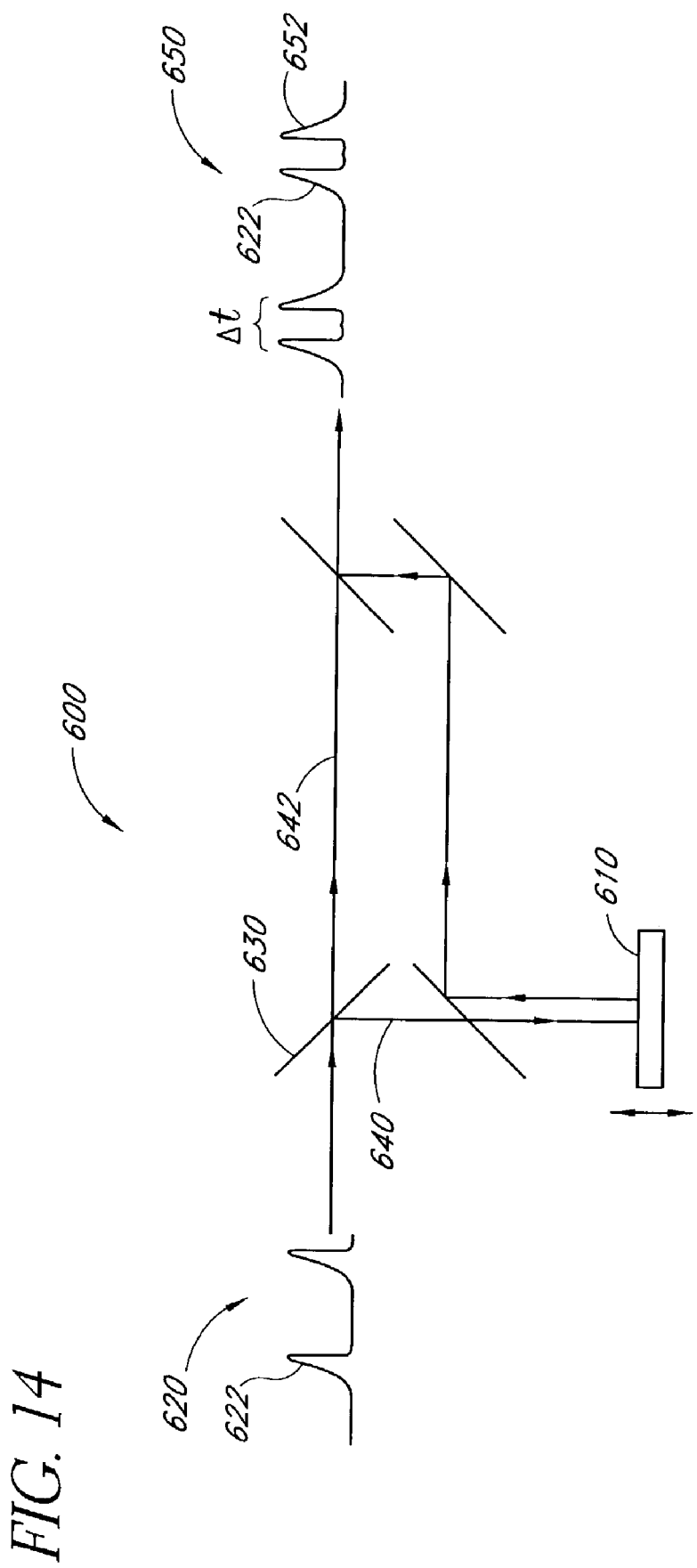
FIG. 14 schematically illustrates a general configuration for converting a periodically repeated sequence of pulses into a periodically repeated sequence of symmetric pulses using a movable phase conjugative mirror.

FIG. 14 schematically illustrates a general configuration 600 for converting a periodically repeated sequence of pulses into a periodically repeated sequence of symmetric pulses using a movable phase conjugative mirror 610. The input pulse sequence 620 comprises a series of original pulses 622. The original pulses 622 can be symmetric or asymmetric. Each of these original pulses 622 is split by the beamsplitter 630 into two portions 640, 642, with one portion 640 being reflected by a phase conjugate mirror 610. In certain embodiments, the phase conjugate mirror 610 comprises an apparatus as schematically illustrated by FIG. 11 in which the input pulse 310 is used to generate the output pulse 320. In certain other embodiments, the phase conjugate mirror 610 comprises an apparatus as schematically illustrated by FIGS. 12A and 12B in which the input pulse 310 is used to generate the output pulse 390. These portions 640, 642 are then combined to form a symmetric composite waveform 650 comprising the temporal waveforms of the original pulses 622 and of the corresponding phase conjugate (time-reversed) pulses 652. The amount of delay $\Delta t$ between an original pulse 622 and the corresponding time-reversed pulse 652 in the symmetric pulse sequence 650 is adjustable by moving the phase conjugative mirror 610.

The symmetric composite waveform 650 has the following form:

$$I_{symmetric}(t) = I\left(-t - \frac{\Delta t}{2}\right) + I\left(t - \frac{\Delta t}{2}\right) \quad (17)$$

where $\Delta t$ is the variable time delay between the time-reversed pulse 652 and the original pulse 622. The Fourier transform of Equation 17 is given by:

$$\tilde{I}_{symmetric}(f) = \tilde{I}(-f)e^{jf\frac{\Delta t}{2}} + \tilde{I}(f)e^{-jf\frac{\Delta t}{2}}. \quad (18)$$

Since I(t) is real, $|\tilde{I}(f)|=|\tilde{I}(-f)|$ and $\phi(f)=-\phi(f)$, where $\tilde{I}(f)$ has been defined as:

$\tilde{I}(f)=|\tilde{I}(f)|e^{j\phi(f)}$.

Using these identities, together with Equations 16 and 18, the Fourier transform of the autocorrelation function corresponding to the symmetric composite waveform 650 has the following form:

$$\overline{A}_{PMT\_double}(f) = 2|\eta|^2|\tilde{I}(f)|^2|1+\cos(2\phi(f)-f\Delta t)|. \quad (19)$$

In embodiments in which $\overline{A}_{PMT\_double}$ is real and greater than zero for all frequencies $\omega$ (i.e., there are no zero crossings of $\overline{A}_{PMT\_double}$ from the cosine term), then the inverse Fourier transform of Equation 20 provides the intensity of the symmetric pulse sequence 650 without any ambiguity. Once the intensity of the symmetric pulse sequence 650 is calculated in this way, the intensity of the original pulse can be found by separating the pulse 650 in the middle.

Figure 15:
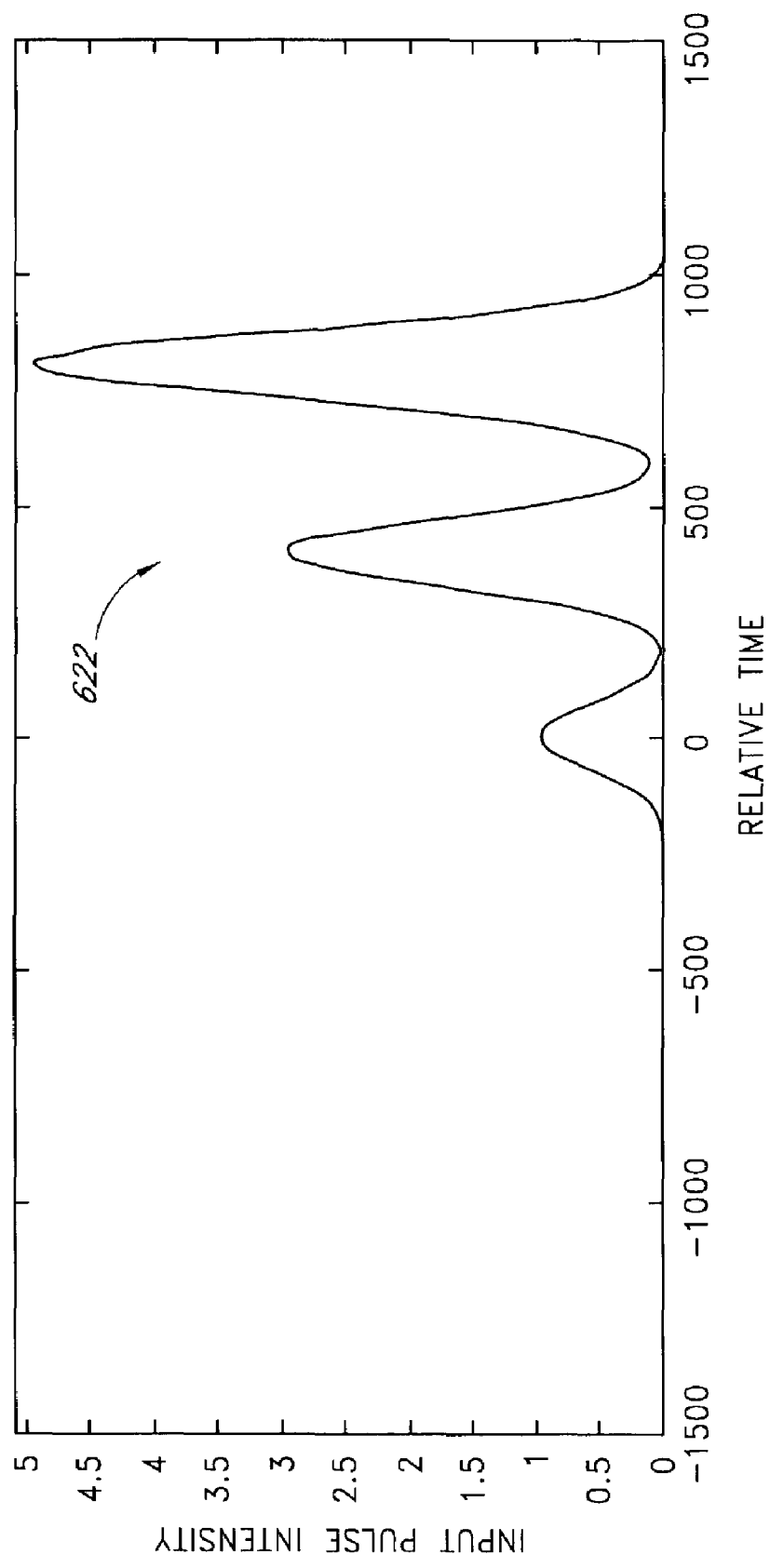
FIG. 15 illustrates an exemplary temporal waveform (in units of W/m$^2$) of an asymmetric input pulse compatible with embodiments of the present invention.
Figure 16:
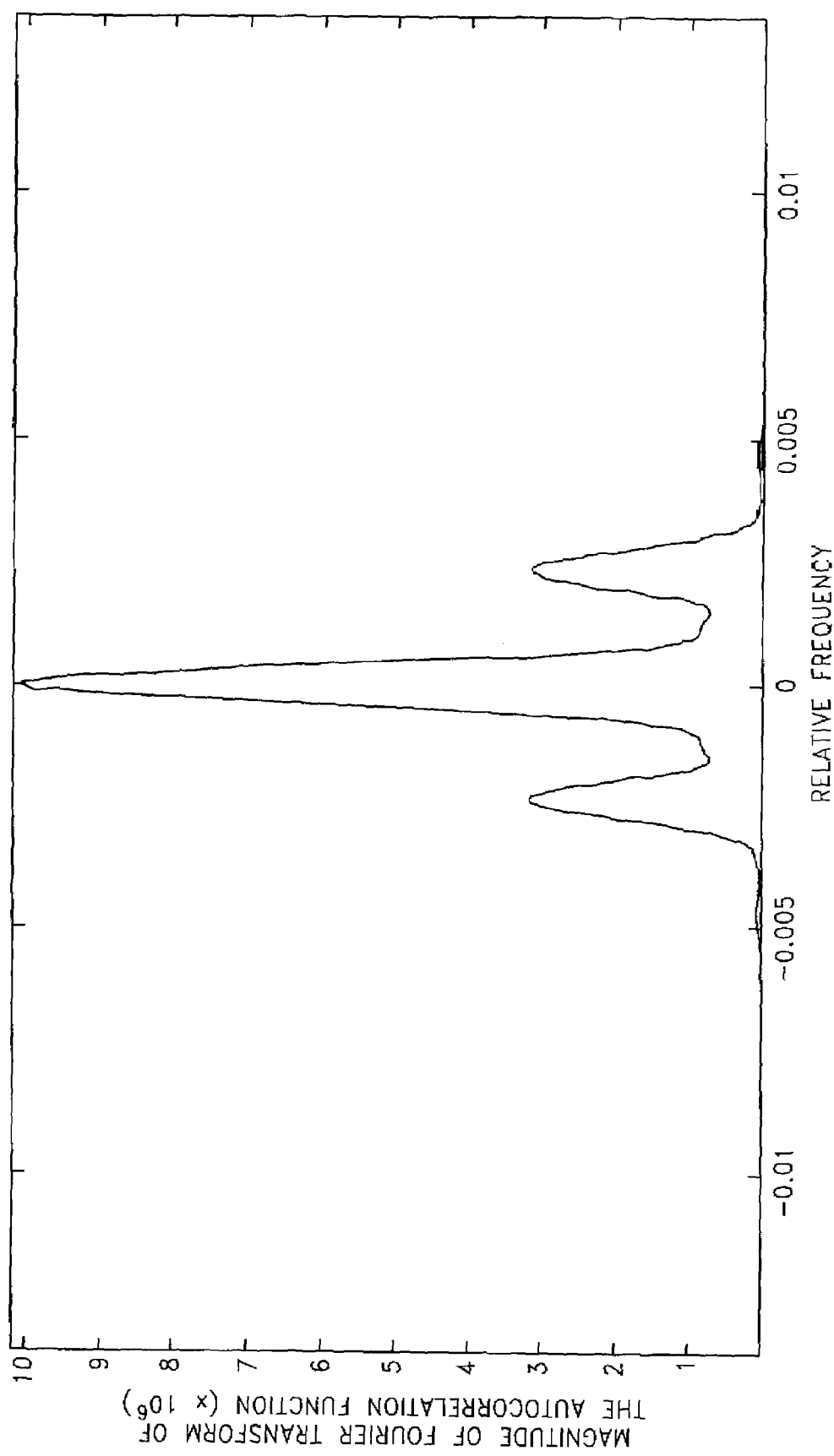
FIG. 16 illustrates the magnitude of the Fourier transform (unitless) of the autocorrelation function corresponding to the temporal waveform of FIG. 15.

FIG. 15 illustrates an exemplary temporal waveform of an input pulse 622 compatible with embodiments of the present invention. The autocorrelation technique commonly used to estimate the temporal profile of an optical pulse is applied to this input pulse as follows. By using the configuration schematically illustrated in FIG. 13, the autocorrelation function (Equation 15) corresponding to the temporal waveform is measured. The magnitude of the Fourier transform of the signal $\overline{A}_{PMT\_single}(\tau)$ recorded by the photomultiplier tube 580 is schematically illustrated in FIG. 16. The frequency $f$ shown in FIG. 16 is $1/\tau$, and is not to be confused with the optical frequency.

Figure 17:
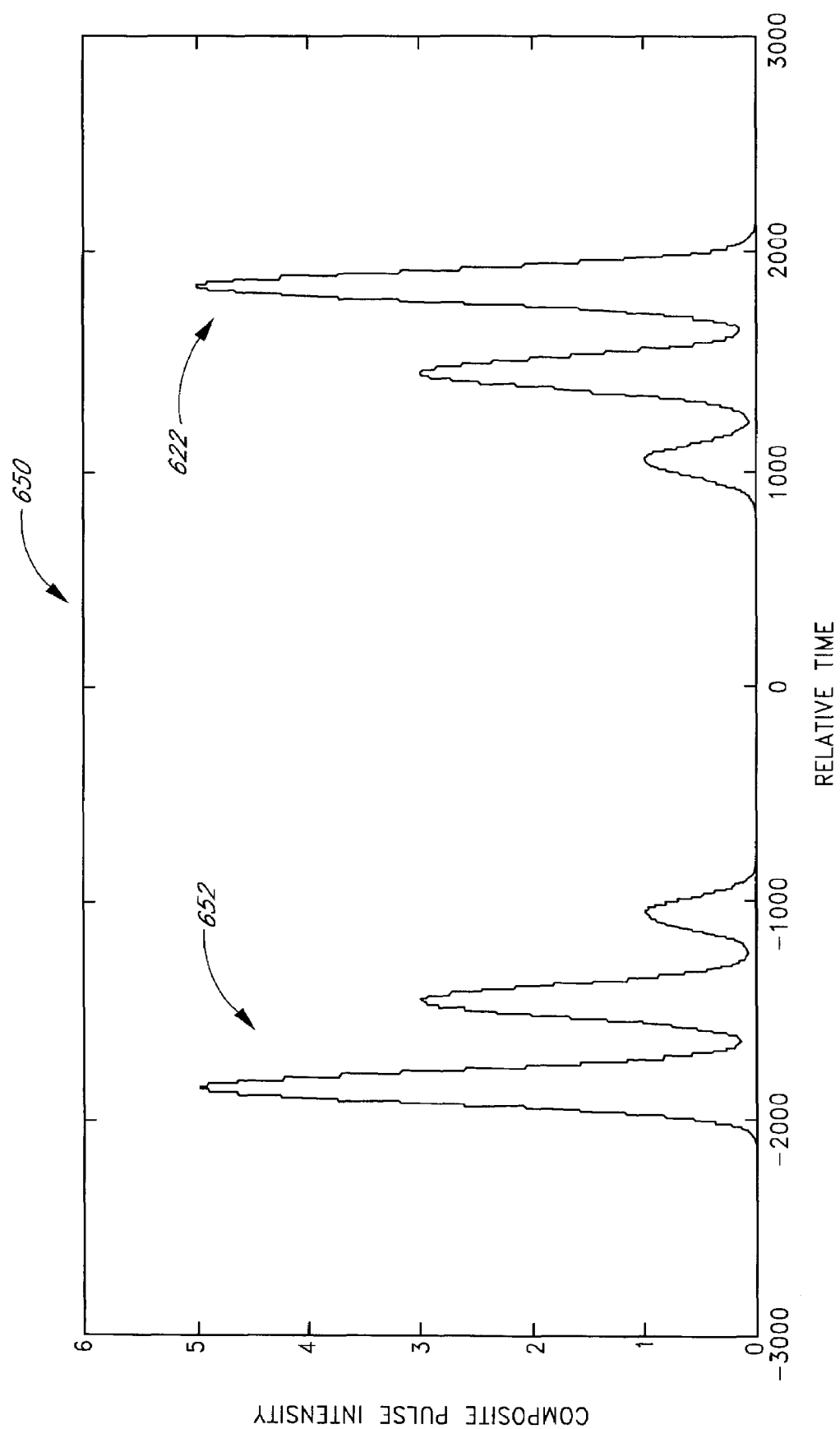
FIG. 17 illustrates the symmetric composite waveform (in units of W/m²) corresponding to the temporal waveform of FIG. 15.

In the following, an embodiment is illustrated analytically by showing the result of numerical simulations using the input pulse of FIG. 15. First, the time-reversal of the input pulse is obtained using one of the phase conjugate mirror schemes described above. FIG. 17 illustrates the symmetric composite waveform 650 defined by Equation 17, which is obtained by combining the input pulse and the time-reversed pulse. The symmetric composite waveform 650 comprises the temporal waveform of the original pulse 622 of FIG. 14 plus the time-reversed temporal waveform of the corresponding time-reversed pulse 652, separated by some time delay.

Figure 18:
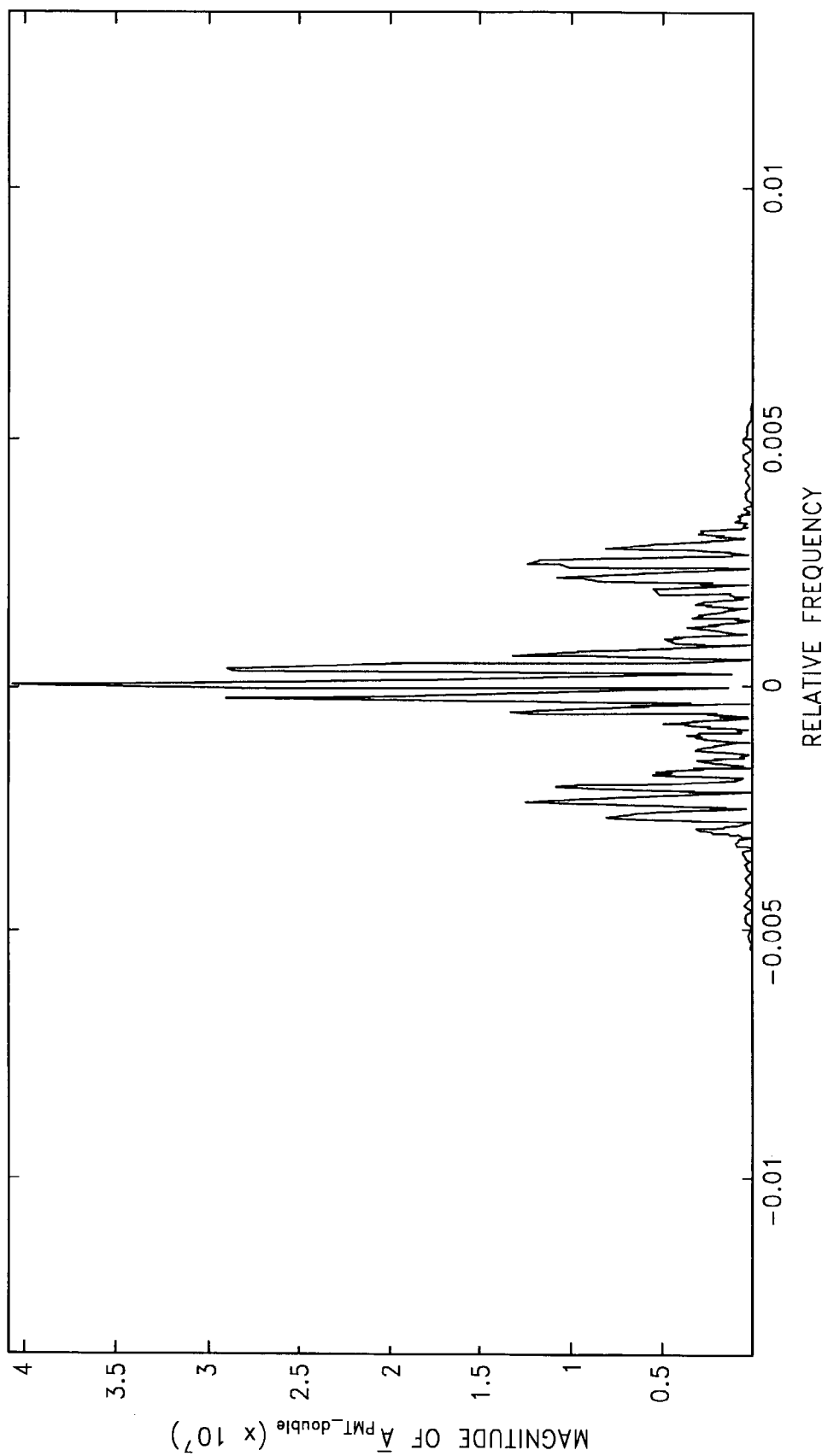
FIG. 18 illustrates the magnitude of the Fourier transform (unitless) of the autocorrelation function of the symmetric composite waveform of FIG. 17.

In the second step, the autocorrelator of FIG. 13 is used to generate the autocorrelation function corresponding to the symmetric composite waveform 650. FIG. 18 illustrates the magnitude of $\overline{A}_{PMT\_double}(f)$ (expressed by Equation 19), which is the Fourier transform of the measured $A_{PMT\_double}(\tau)$. The envelope of the Fourier transform magnitude of the measured $A_{PMT\_double}(\tau)$ is a scaled version of the Fourier transform magnitude (as shown in FIG. 16) of the signal $A_{PMT\_single}(\tau)$ measured by the photomultiplier tube 580. Therefore, $|\tilde{I}(f)|^2$ or $|\tilde{I}(f)|$ can be recovered from only the envelope of the Fourier transform magnitude of the measured $A_{PMT\_double}(\tau)$ (i.e., from only the measurement of the autocorrelation function of the symmetric composite waveform 650). This result implies that the measurement of the autocorrelation function for the single pulse as schematically illustrated in FIG. 15 is redundant. However, since it does not add complexity to the measurement, certain embodiments also comprise obtaining $|\tilde{I}(f)|^2$ data from a separate source for error checking purposes.

In the third step, the function $g(f)=1+\cos(2\phi(f)-f\Delta t)$ is determined by dividing both sides of Equation 19 by $|\tilde{I}(f)|^2$. From the knowledge of $g(f)-1$, the function $$\left|\cos\left(\varphi(f) - f\frac{\Delta t}{2}\right)\right|$$

can be determined. Using Equation 18, the Fourier transform of the symmetric temporal waveform can be expressed as:

$$\tilde{I}_{symmetric}(f) = 2|\tilde{I}(f)|\cos\left(\varphi(f) - f\frac{\Delta t}{2}\right). \quad (20)$$

Therefore, since $|\tilde{I}(f)|$ is known from FIG. 16 or from the envelope of FIG. 18, the only information needed to determine $I_{symmetric}(t)$ directly by taking the inverse Fourier transform of Equation 20 is the knowledge of cos $$\cos\left(\varphi(f) - f\frac{\Delta t}{2}\right).$$

To determine the function cos $$\cos\left(\varphi(f) - f\frac{\Delta t}{2}\right)$$

from the function $$\left|\cos\left(\varphi(f) - f\frac{\Delta t}{2}\right)\right|,$$

two possible cases can be analyzed. In the first case, if there are no zero crossings of the term $$\left|\cos\left(\varphi(f) - f\frac{\Delta t}{2}\right)\right|,$$

then there is no ambiguity due to the absolute value sign since intensity has to be non-negative ($-I_{symmetric}(t)$ is not a possible solution). In the second case, if there are some zero crossings of the term $$\left|\cos\left(\varphi(f) - f\frac{\Delta t}{2}\right)\right|,$$

the sign ambiguities of the cosine term between the zero crossings can be removed by using a property of Fourier transforms. For a real and symmetric function such as $I_{symmetric}(t)$, the Fourier transform $\bar{I}_{symmetric}(f)$ is equivalent to the Hartley transform $I_{symmetric}^{Ha}(f)$. Therefore, the magnitude of the Hartley transform of $I_{symmetric}(t)$ (i.e., $$|I_{symmetric}^{Ha}(f)| = |\bar{I}_{symmetric}(f)| = 2|\bar{I}(f)|\left|\cos\left(\varphi(f) - f\frac{\Delta t}{2}\right)\right|$$

can be determined from the knowledge of $$\left|\cos\left(\varphi(f) - f\frac{\Delta t}{2}\right)\right|$$

and $|\bar{I}(f)|$. For a real and compact support function (i.e., one that equals zero outside a finite region), such as $I_{symmetric}(t)$, the intensity of the Hartley transform is enough to uniquely recover the original function. See, e.g., N. Nakajima in *Reconstruction of a real function from its Hartley-transform intensity*, Journal of the Optical Society of America A, Vol. 5, 1988, pages 858–863, and R. P. Millane in *Analytic Properties of the Hartley Transform and their Implications*, Proceedings of the IEEE, Vol. 82, 1994, pages 413–428, both of which are incorporated in their entirety by reference herein.

Figure 19A:
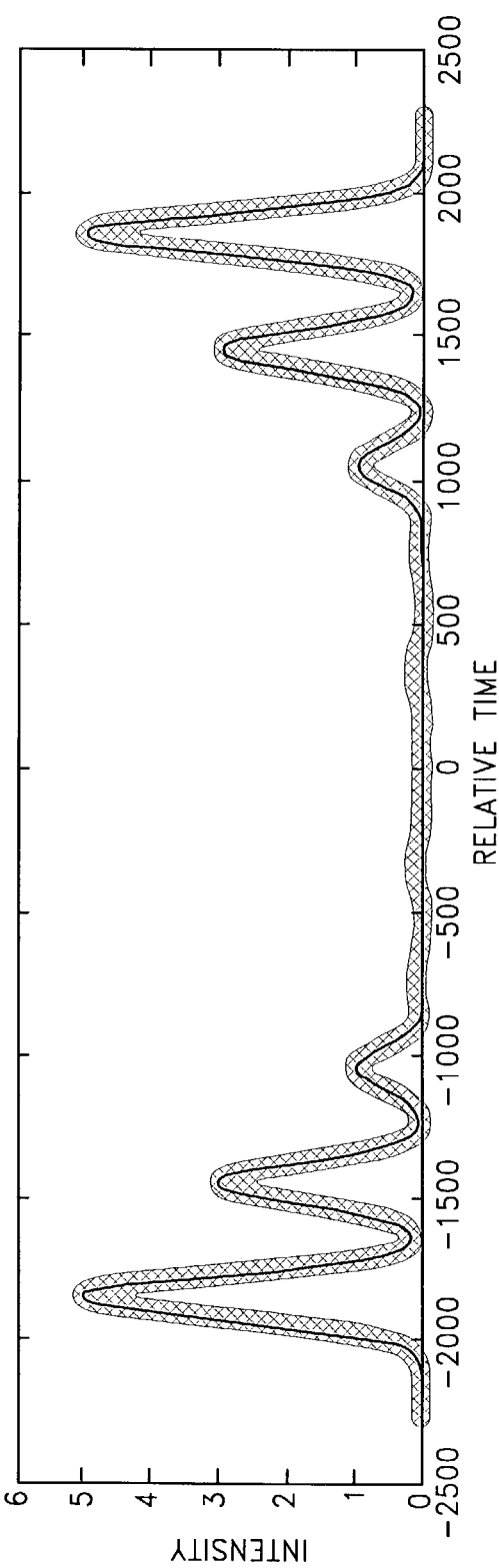
FIG. 19A illustrates the recovered symmetric temporal waveform (in units of W/m²).
Figure 19B:
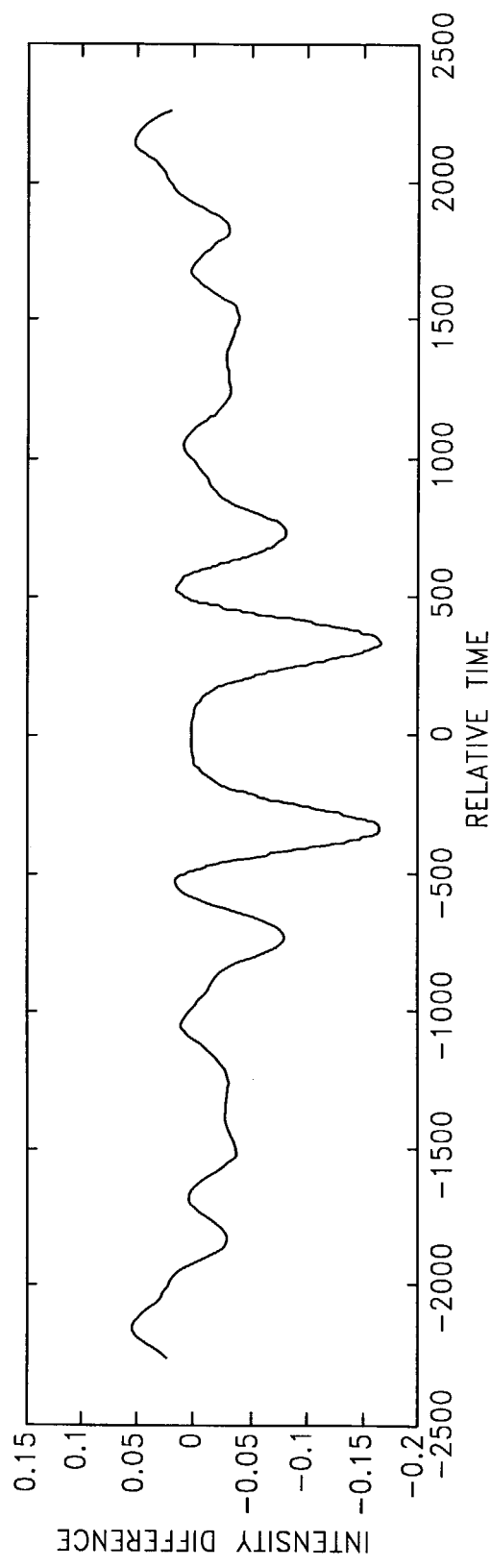
FIG. 19B illustrates the difference (in units of W/m²) between the recovered symmetric temporal waveform and the temporal waveform of the original pulse.

FIG. 19A illustrates the recovered symmetric temporal waveform and FIG. 19B illustrates the difference between the recovered symmetric temporal waveform and the temporal waveform of the original pulse (as shown in FIG. 17). As illustrated by FIG. 19B, the two waveforms are in excellent agreement (within approximately 0.15) with one another. The difference shown in FIG. 19B is in fact just a numerical calculation artifact, which can be improved with increased accuracy. Thus, the configuration schematically illustrated in FIG. 13 is capable of recovering ultra-short temporal waveforms unambiguously when used with a time-reversal scheme, such as that illustrated by FIG. 14.

Figure 20:
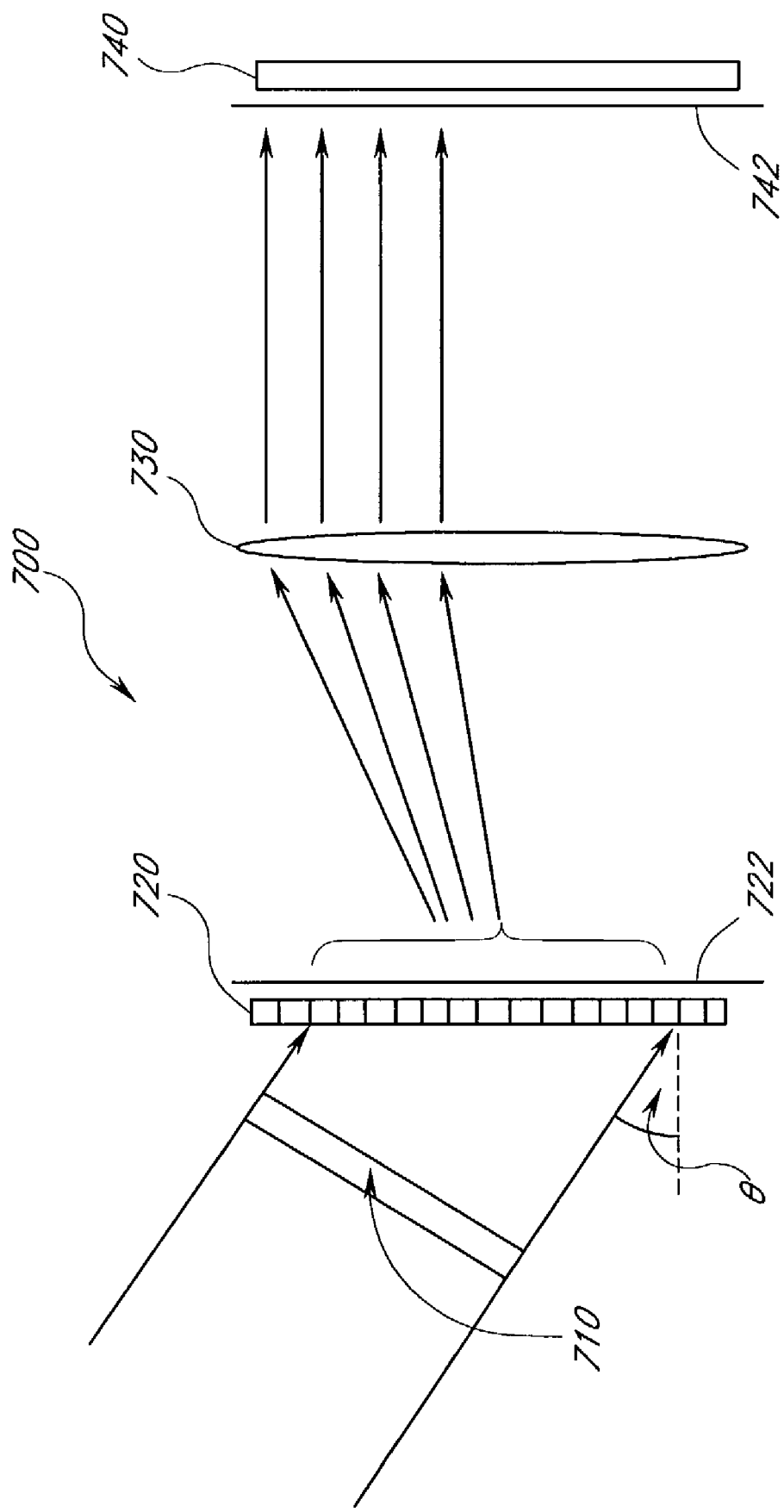
FIG. 20 schematically illustrates a system for another embodiment for determining the temporal waveform of a laser pulse.

FIG. 20 schematically illustrates a system 700 for another embodiment for determining the temporal waveform of a laser pulse. The input pulse 710 impinges onto a grating 720 which disperses the input pulse 710 into its spectral components. A lens 730 recollimates the spectral components and images them onto different elements of a CCD imaging device 740.

An arbitrary input pulse 710 has the following form:

$$u_s(t) = \tilde{u}_s(t)e^{j\omega_c t} \qquad (21)$$

where $\tilde{u}_s(t)$ is the complex envelope function and $\omega_c$ is the carrier frequency. Equation 21 can be rewritten as:

$$u_s(t) = \int \tilde{U}_s(\omega - \omega_c)e^{j\omega t}d\omega \qquad (22)$$

where $\tilde{U}_s(\omega)$ denotes the Fourier transform of $\tilde{u}_s(t)$. The input pulse 710 is decomposed by the grating 720 into several monochromatic plane waves with amplitudes $\tilde{U}_s(\omega-\omega_c)$. By finding the response of the system 700 to each individual harmonic component (i.e. $\tilde{U}_s(\omega-\omega_c)e^{j\omega t}$), the overall response of the system 700 can be determined using the integral given in Equation 22.

The field of a single harmonic $\tilde{U}_s(\omega-\omega_c)e^{j\omega t}$ at the plane 722 immediately after being dispersed by the grating 720 can be written in the following form:

$$\tilde{U}_{1s}(x;\omega,t) = \tilde{U}_s(\omega-\omega_c)e^{j\omega t}w(x)e^{-jx\left(\frac{\omega-\omega_c}{c}\sin\theta\right)} \qquad (23)$$

where w(x) is the pupil function of the optical field on the grating 720, c is the speed of light, x is the coordinate along the plane 722, and θ is the incident angle of the input pulse 710 to the grating 720. This form of the single harmonic field is described by P. C. Sun et al. in *Femtosecond Pulse Imaging: Ultrafast Optical Oscilloscope*, Journal of the Optical Society of America, Vol. 14, 1997, pages 1159–1170, which is incorporated in its entirety by reference herein.

The last exponential term of Equation 23 accounts for the diffraction experienced by the spectral components of the input pulse 710 due to the grating 720, assuming only first-order diffraction. The grating 720 is arranged such that the first diffraction order for the spectral component at $\omega=\omega_c$ propagates along the direction of the optical axis of the system 700. The lens 730 transforms the image at the plane 722 into an image at plane 742. The fields at the two planes 722, 742 are related by a spatial Fourier transform. By taking the spatial Fourier transform of Equation 23, the field at the plane 742 can be written as:

$$\tilde{U}_{2s}(f_{x'};\omega,t) = \tilde{U}_s(\omega-\omega_c)e^{j\omega t}W\left(f_{x'} + \frac{\omega-\omega_c}{2\pi c}\sin\theta\right) \qquad (24)$$

where $W(f_{x'})$ is the spatial Fourier transform of $w(x)$. $x'$ is the coordinate along the plane 742, and $f_{x'}$ is the spatial frequency which can be written as:

$$f_{x'} = \frac{\omega x'}{2\pi c F} \quad (25)$$

where F is the focal length of the lens.

The total response of the system 700 is the spectral decomposition of the field $u_s(t)$ of the input pulse 710 and can be found by integrating Equation 24 over the frequency range, i.e.,:

$$u_{2s}(x';t) = \int \tilde{U}_{2s}(x';\omega,t) d\omega \quad (26)$$

By using the paraxial approximation and by assuming a large illumination window $w(x)$, the total response given by Equation 27 can be simplified to the following form:

$$u_{2s}(x';t) \approx \tilde{U}_s\left(-\frac{x'\omega_c}{F\sin\theta}\right) w\left(\left[1 - \frac{x'}{F\sin\theta}\right]\frac{ct}{\sin\theta}\right) e^{j\omega_c\left(\left[1-\frac{x'}{F\sin\theta}\right]t\right)} \quad (27)$$

By generating a phase conjugate pulse as schematically illustrated in FIG. 14, the total output waveform can be expressed as: $u_{total}(t) = u_s(t) + u_{PC}(t-\Delta t)$, where PC denotes "phase conjugate." The function $u_{PC}(t)$ is dependent on the type of phase conjugate mirror used to generate the phase conjugate pulses. For phase conjugate pulses formed using pulse-pumped FWM, the total field $u_{total}(t)$ can be expressed, using Equation 10, in the following form:

$$u_{total}(t) = (\tilde{u}_s(t) + \tilde{u}_s^*(-t-\Delta t)) e^{j\omega_c t} \quad (28)$$

where $\Delta t$ is the time delay between the original pulse and its corresponding phase conjugate pulse. Feeding this total field into the system 700 illustrated in FIG. 20, the resultant image field at the plane 742 of the CCD imaging device 740, using Equation 27, can be expressed as:

$$u_{total,2}(x';t) \approx \tilde{U}_s\left(-\frac{x'\omega_c}{F\sin\theta}\right) w\left(\left[1 - \frac{x'}{F\sin\theta}\right]\frac{ct}{\sin\theta}\right) e^{j\omega_c\left(\left[1-\frac{x'}{F\sin\theta}\right]t\right)} + \tilde{U}_s^*\left(-\frac{x'\omega_c}{F\sin\theta}\right) w\left(\left[1 - \frac{x'}{F\sin\theta}\right]\frac{ct}{\sin\theta}\right) e^{j\omega_c\left(\left[1-\frac{x'}{F\sin\theta}\right]t\right)} e^{j\Delta t\left(-\frac{x'\omega_c}{F\sin\theta}\right)} \quad (29)$$

The CCD imaging device 740 at the plane 742 is responsive to intensity, which can be written as:

$$I(x') = \int |u_{total,2}(x';t)|^2 dt. \quad (30)$$

Defining $\tilde{U}_s(\omega) = |\tilde{U}_s(\omega)| e^{j\Phi(\omega)}$ and $A = -F\sin\theta$, Equation 30 can be rewritten as:

$$I_{double}(x') = 2\left(\int \left|w\left(\left[1 + \frac{x'}{A}\right]\frac{ct}{\sin\theta}\right)\right|^2 dt\right) \left|\tilde{U}_s\left(\frac{x'\omega_c}{A}\right)\right|^2 \left[1 + \cos\left(2\Phi\left(\frac{x'\omega_c}{A}\right) - \Delta t\frac{x'\omega_c}{A}\right)\right]. \quad (31)$$

Furthermore, Equation 31 can be rewritten as:

$$I_{double}(x') = 2G(x')\left|\tilde{U}_s\left(\frac{x'\omega_c}{A}\right)\right|^2 \left[1 + \cos\left(2\Phi\left(\frac{x'\omega_c}{A}\right) - \Delta t\frac{x'\omega_c}{A}\right)\right]. \quad (31)$$

with $$G(x') = \int \left|w\left(\left[1 + \frac{x'}{A}\right]\frac{ct}{\sin\theta}\right)\right|^2 dt.$$

Equation 32 is very similar to Equation 19, which was obtained for embodiments utilizing the intensity correlator of FIG. 13. Furthermore, the intensity profile on the CCD imaging device 740 for a single pulse $u_s(t)$ can be expressed as:

$$I_{single}(x') = G(x')\left|\tilde{U}_s\left(\frac{x'\omega_c}{A}\right)\right|^2. \quad (33)$$

Equation 33 is also very similar to Equation 16, which was derived above in relation to the intensity correlator embodiment as shown in FIG. 13.

Figure 21A:
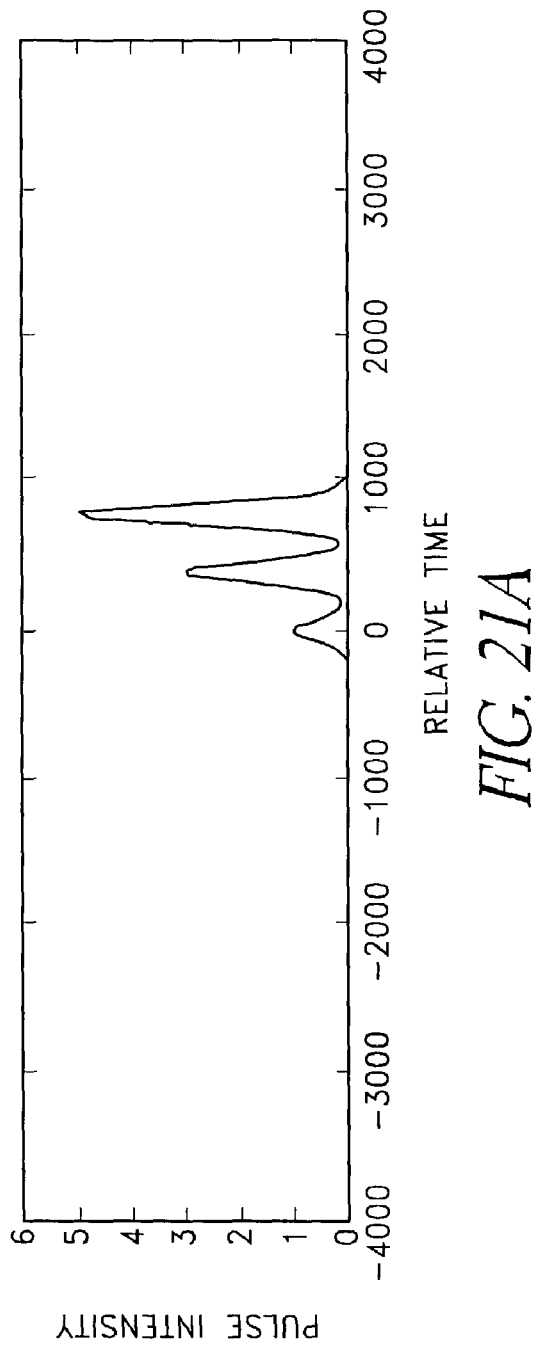
FIGS. 21A and 21B illustrate the magnitude (in units of W/m²) and phase of an arbitrary asymmetric complex envelope function to be characterized.
Figure 21B:
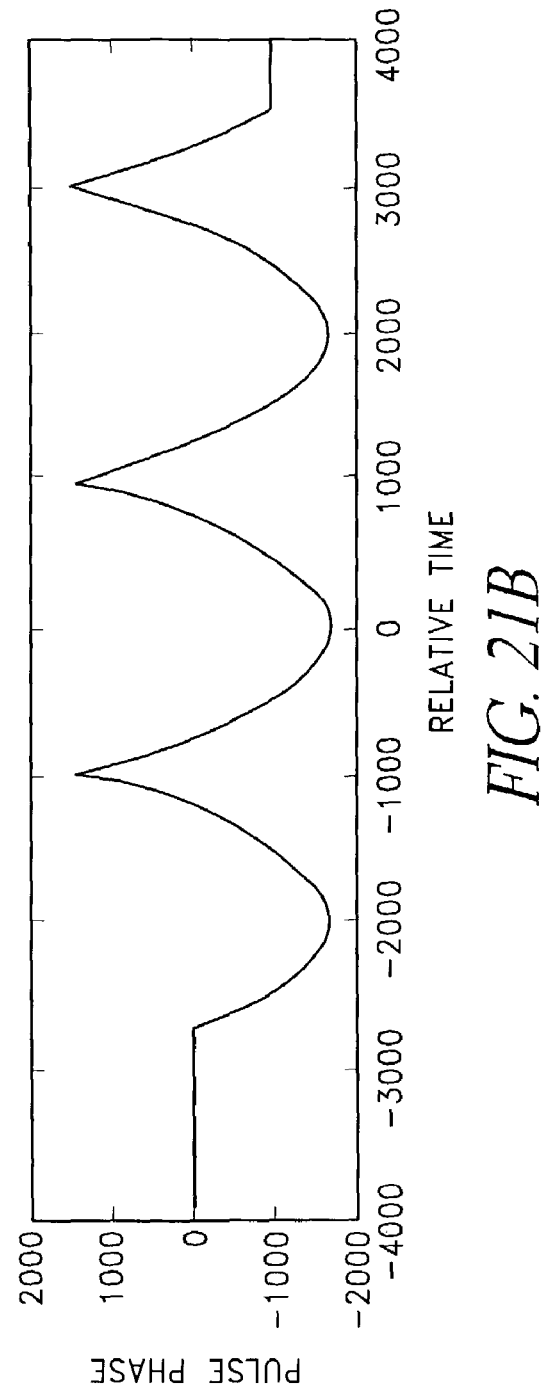
Figure 22:
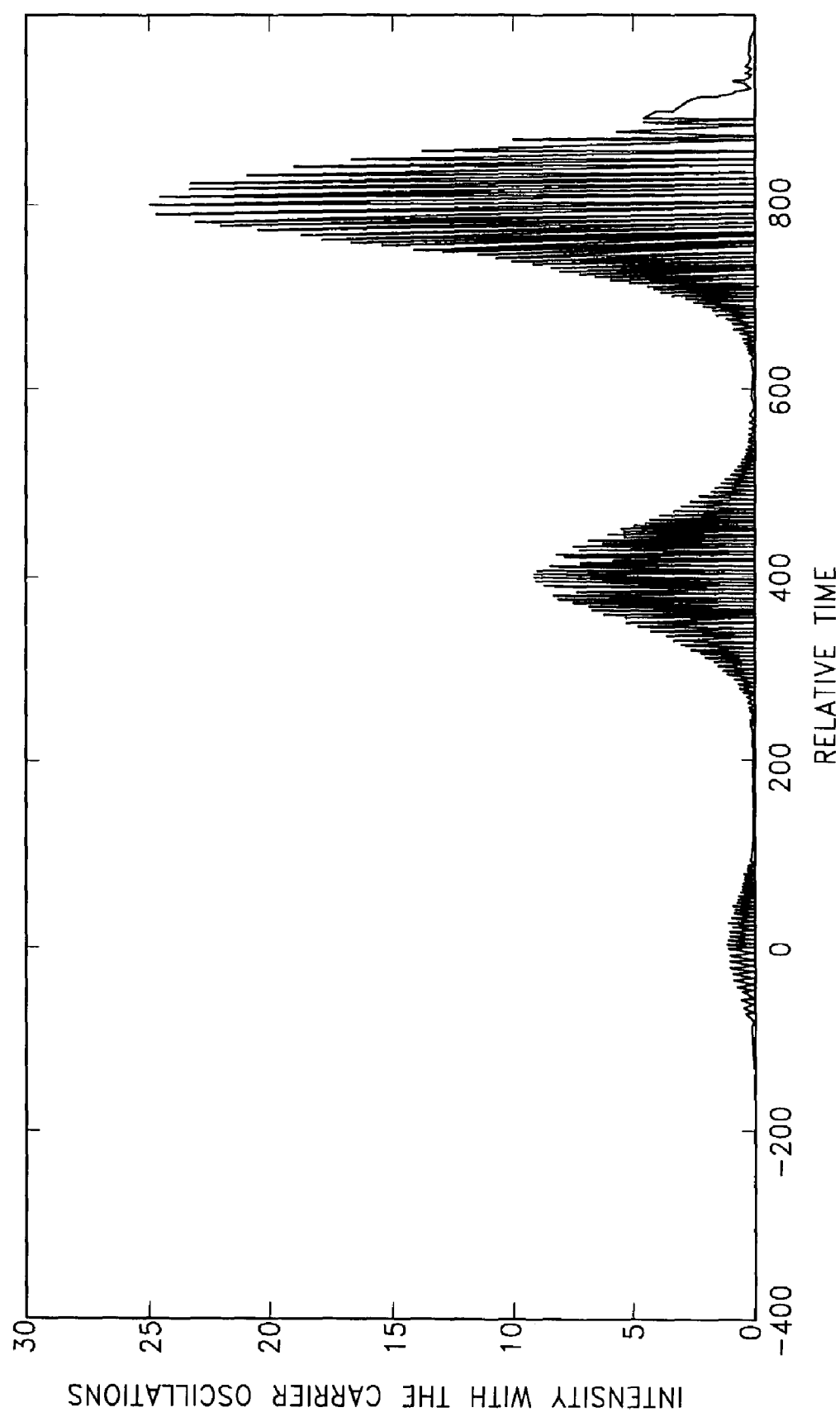
FIG. 22 illustrates the intensity profile (in units of W/m²) for the asymmetric complex envelope function of FIG. 21A with the carrier frequency oscillations.
Figure 23:
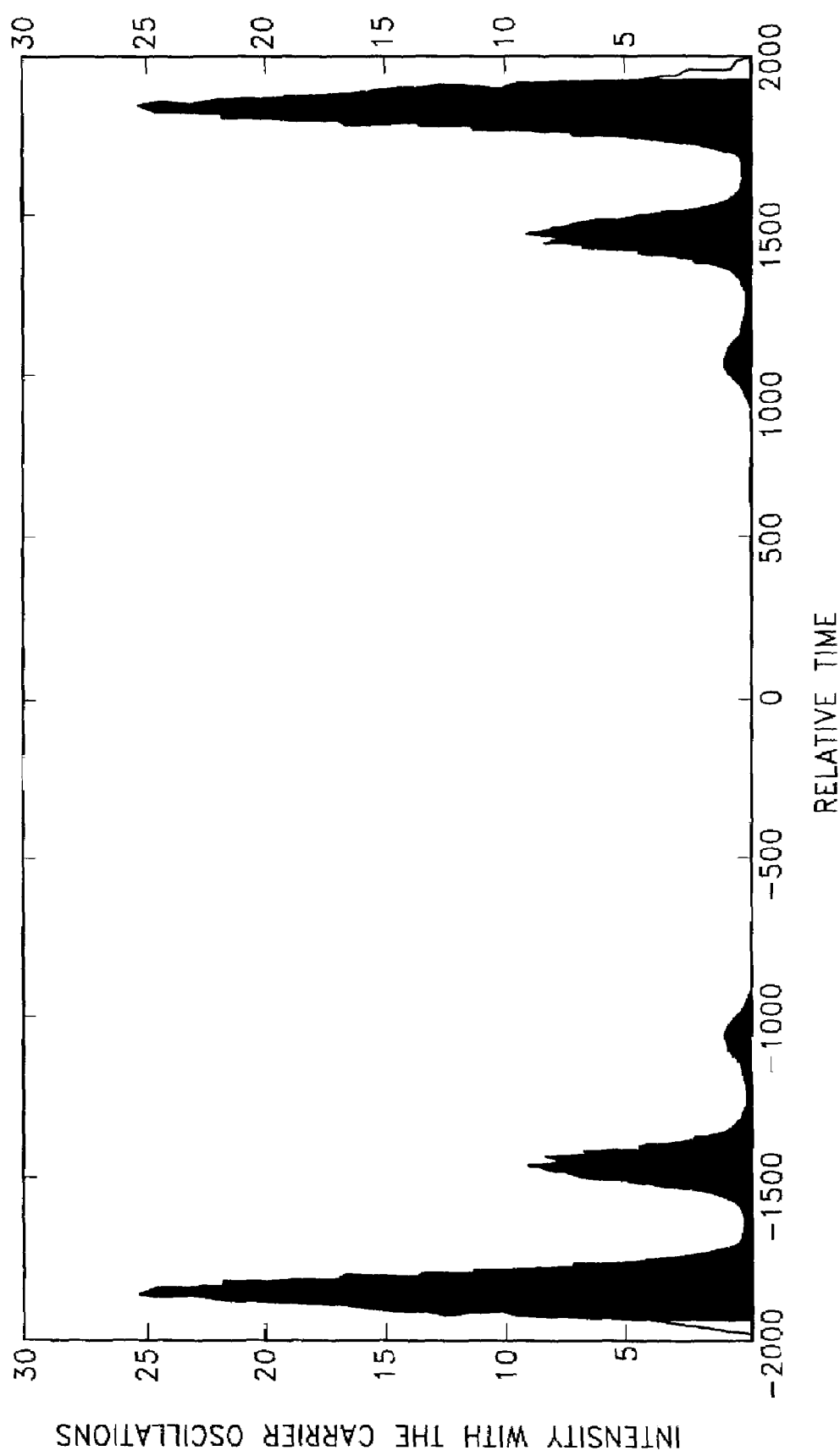
FIG. 23 illustrates the symmetric temporal waveform (in units of W/m²) with the carrier frequency corresponding to the asymmetric complex envelope function of FIG. 22.

To recover the complex envelope function $\tilde{u}_s(t)$, as defined in Equation 21, the same algorithm described above for recovering $I(t)$ can be applied. This process is illustrated in the FIGS. 21 through 26 using computer-generated simulations. FIGS. 21A and 21B illustrate the magnitude and phase of an arbitrary asymmetric complex envelope function $\tilde{u}_s(t)$ to be characterized, respectively. (FIG. 21A is the same input pulse as shown in FIG. 15). FIG. 22 illustrates the intensity profile for this complex field, including the carrier frequency oscillations. Note that FIG. 15 described above did not include the carrier frequency oscillations and was just the envelope of the intensity. In a first step, the general configuration 600 of FIG. 14 is used to generate the symmetric temporal waveform whose complex envelope function is defined by Equation 28. FIG. 23 illustrates the symmetric temporal waveform, including the carrier frequency, generated by this first step. The symmetric temporal waveform comprises the temporal waveform of the original pulse plus the time-delayed temporal waveform of the time-reversed pulse.

Figure 24A:
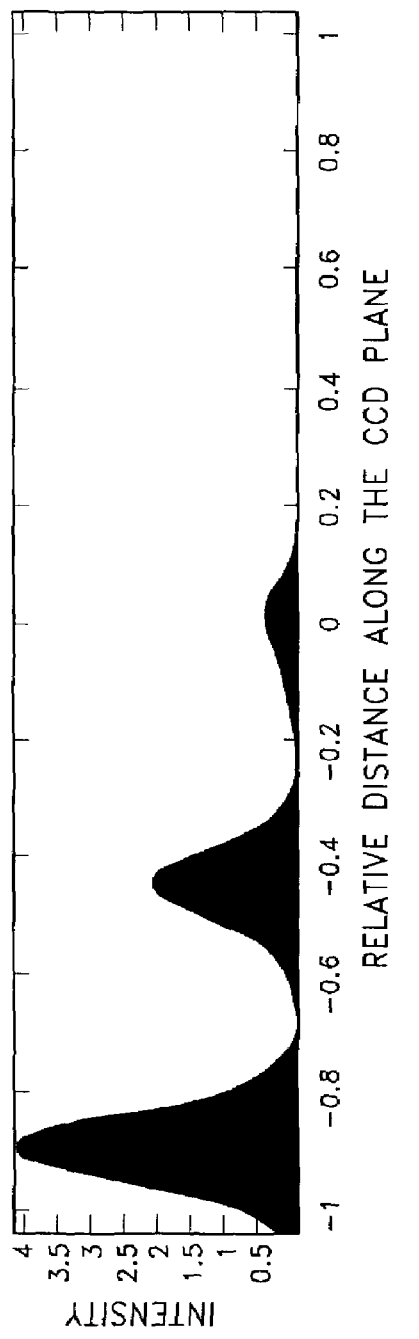
FIGS. 24A and 24B illustrate the detected intensity (in units of W/m²) on the CCD imaging device for the symmetric pulse of FIG. 23, and the single pulse of FIG. 22, respectively.
Figure 24B:
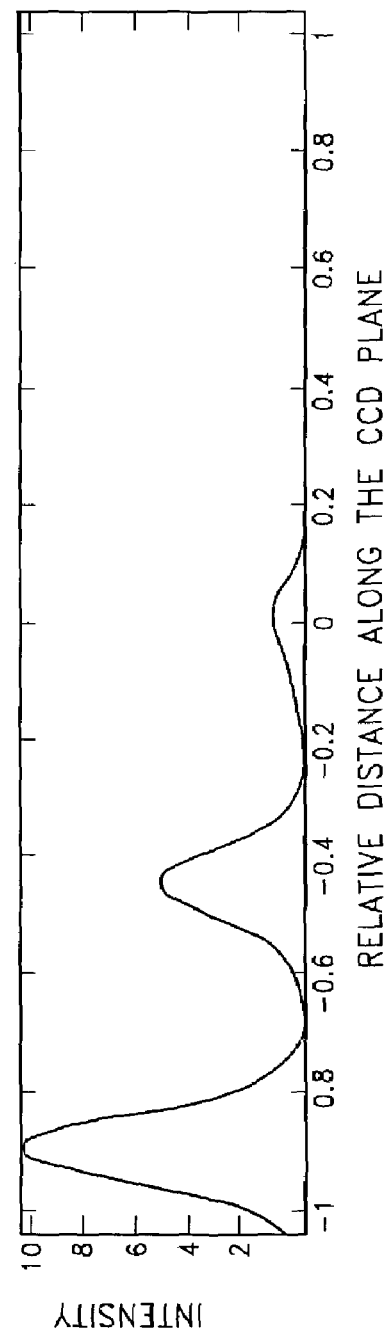

In a second step, the system of FIG. 20 is used to measure the Fourier transform of the symmetric pulse with the CCD imaging device. FIG. 24A illustrates the detected intensity I(x') on the CCD imaging device at the plane 742 for the symmetric pulse of FIG. 23. The intensity I(x') was calculated using Equation 32. For comparison, FIG. 24B shows the detected intensity I(x') on the CCD imaging device at the plane 742 using the original pulse of FIG. 22, which is a prior art measurement technique. The intensity I(x') was calculated using Equation 33.

Figure 25A:
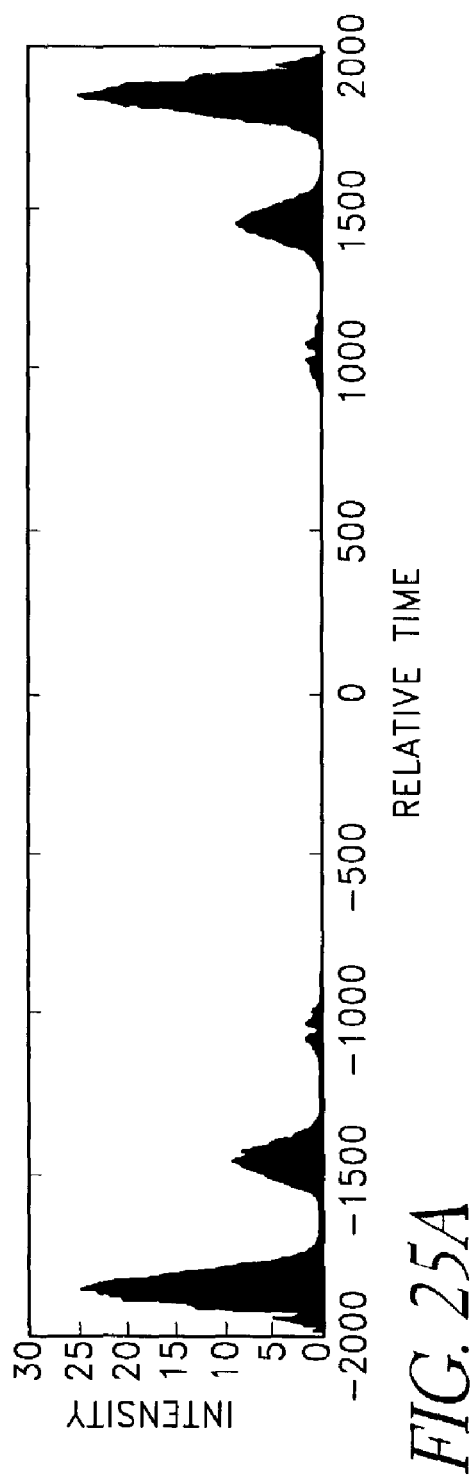
FIGS. 25A and 25B illustrate the recovered symmetric temporal waveform and the original temporal waveform (in units of W/m²), respectively, including the carrier frequencies.
Figure 25B:
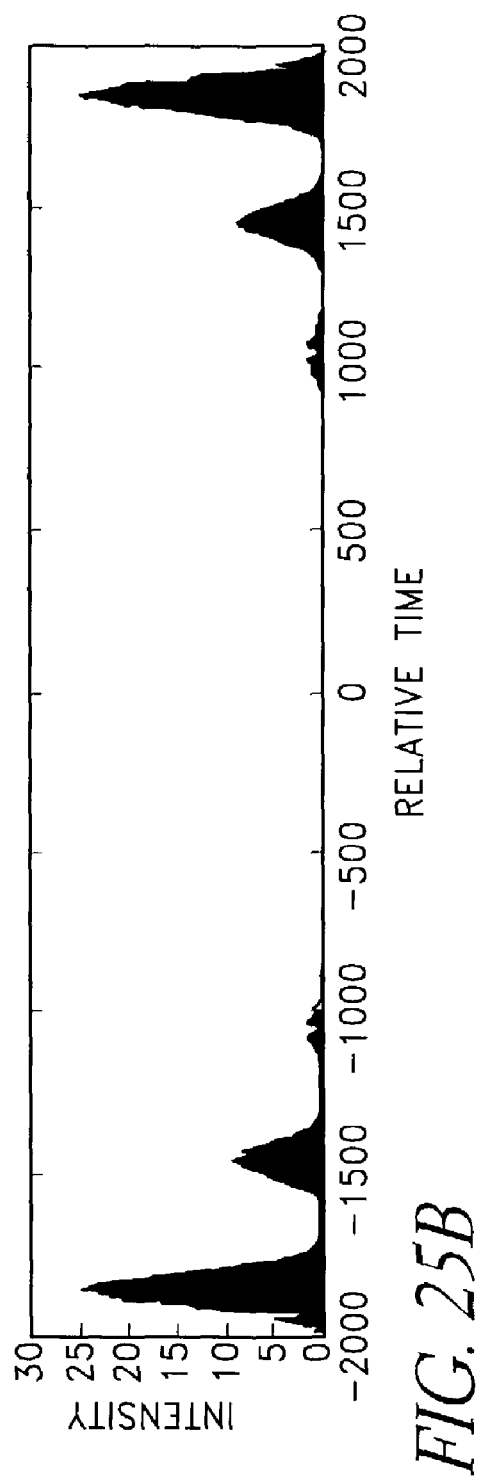
Figure 26:
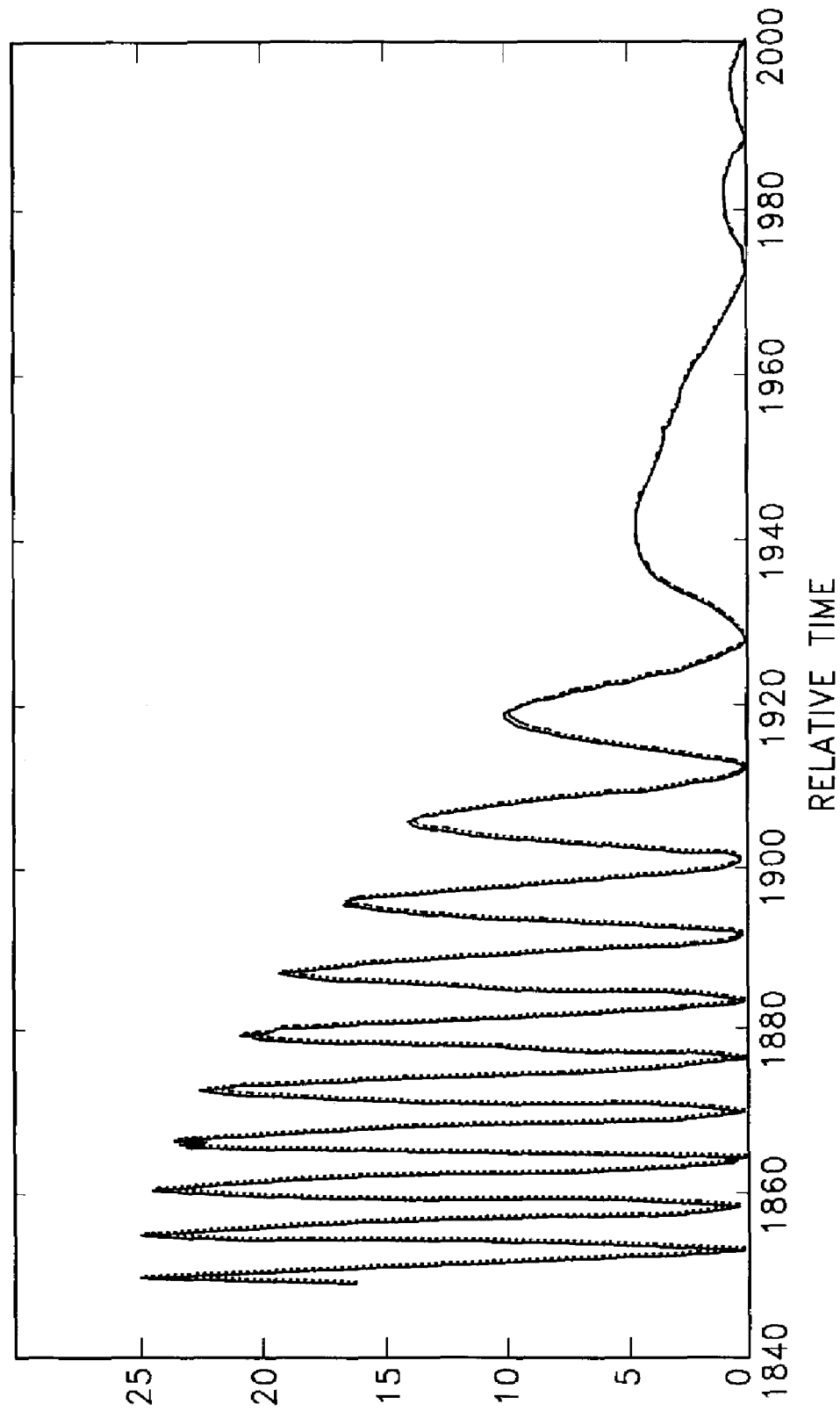
FIG. 26 illustrates the waveforms of FIGS. 25A and 25B (in units of W/m²) overlaid with one another in an expanded time frame for comparison purposes.

In a third step, and as discussed above in relation to determining I(t) using the intensity correlation configuration of FIG. 13, the CCD image (FIG. 24A) is used to calculate numerically both amplitude and the phase of the Fourier transform of the complex envelope function $\tilde{u}_s(t)$. One can calculate the complex envelope function $\tilde{u}_s(t)$ using inverse Fourier transform once both the amplitude and the phase functions of the Fourier transform are recovered. FIGS. 24A and 24B illustrate the recovered symmetric temporal waveform and the original temporal waveform, respectively, including the carrier frequencies. FIG. 25 illustrates these waveforms overlaid with one another in an expanded time frame for comparison purposes. This comparison establishes that the prediction of the pulse shape made available by this invention is excellent. The discrepancy between the two curves of FIG. 26 is in fact a numerical artifact that can be removed by increasing the computation accuracy.

Therefore, using the same process as described above in relation to Equation 19, the system 700 of FIG. 20 can be used to recover the complex envelope function $\tilde{u}_s(t)$ of any given input pulse using only the Fourier transform amplitude of the symmetrized composite waveform. In addition, both the envelope of the intensity profile I(t) and the underlying optical oscillations are recoverable, as illustrated by FIG. 26. Recovering both the envelope and the underlying oscillations is an improvement with respect to the prior art intensity correlation embodiment described above, which only recovers the envelope of I(t).

This invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. A method of measuring a second-order optical nonlinearity profile of a sample, the method comprising:
   providing the sample having the second-order optical nonlinearity profile;
   placing a surface of the sample in proximity to a surface of a supplemental sample, wherein the sample and supplemental sample form a composite sample having a symmetric second-order optical nonlinearity profile;
   measuring a Fourier transform of the symmetric second-order optical nonlinearity profile; and
   calculating an inverse Fourier transform of the measured Fourier transform, wherein the calculated inverse Fourier transform provides information regarding the second-order optical nonlinearity profile.

2. The method of claim 1, wherein the second-order optical nonlinearity profile is non-symmetric.

3. The method of claim 1, wherein the information comprises the magnitude and sign of the second-order optical nonlinearity profile as a function of depth below the surface of the sample.

4. The method of claim 1, wherein the information comprises the position of the second-order optical nonlinearity profile below the surface of the sample.

5. The method of claim 1, wherein the information comprises whether the second-order optical nonlinearity profile is symmetric or non-symmetric.

6. The method of claim 1, wherein the sample comprises poled silica.

7. The method of claim 1, wherein the sample comprises a nonlinear organic material.

8. The method of claim 1, wherein the sample comprises a nonlinear inorganic material.

9. The method of claim 8, wherein the sample comprises an amorphous material.

10. The method of claim 1, wherein the sample and the supplemental sample have substantially identical second-order nonlinearity profiles.

11. The method of claim 10, wherein the sample and the supplemental sample comprise two portions of a common sample.

12. The method of claim 10, wherein the sample and the supplemental sample are prepared using substantially identical conditions.

13. The method of claim 1, wherein the supplemental sample comprises a reflector.

14. The method of claim 1, wherein placing the sample in proximity to the supplemental sample to form the composite sample comprises sandwiching the sample and the supplemental sample together.

15. The method of claim 14, wherein the sample and the supplemental sample are sandwiched together in an anode-to-anode configuration.

16. The method of claim 14, wherein the sample and the supplemental sample are sandwiched together in a cathode-to-cathode configuration.

17. The method of claim 14, wherein a spacer material is placed between the sample and the supplemental sample.

18. The method of claim 1, wherein measuring the Fourier transform comprises measuring the Maker fringe profile of the composite sample.

19. The method of claim 1, wherein measuring the Fourier transform comprises focusing a pulsed laser beam onto the composite sample at an incident angle, generating a second-harmonic signal, and measuring the generated second-harmonic power as a function of the incident angle.

20. A method of measuring a second-order optical nonlinearity profile of a sample, the method comprising:
    forming a composite sample by placing a surface of the sample in proximity to a surface of a supplemental sample, wherein the composite sample has a symmetric second-order optical nonlinearity profile;
    measuring a Fourier transform of the symmetric second-order optical nonlinearity profile; and
    calculating an inverse Fourier transform of the measured Fourier transform, wherein the calculated inverse Fourier transform provides information regarding the second-order optical nonlinearity profile.

21. A method of measuring a second-order optical nonlinearity profile of a sample, the method comprising:
    forming a composite sample by placing a surface of the sample in proximity to a surface of a supplemental sample;
    measuring a Fourier transform of a second-order optical nonlinearity profile of the composite sample; and
    obtaining information regarding the second-order optical nonlinearity profile of the sample by calculating an inverse Fourier transform of the measured Fourier transform.

* * * * *

UNITED STATES PATENT AND TRADEMARK OFFICE
CERTIFICATE OF CORRECTION

PATENT NO. : 7,133,134 B2
APPLICATION NO. : 10/357275
DATED : November 7, 2006
INVENTOR(S) : Aydogan Ozcan et al.

It is certified that error appears in the above-identified patent and that said Letters Patent is hereby corrected as shown below:

On the title page, item [56]:

On Page 2, Col. 1 ("Other Publications"), Line 36, delete "Milane" and insert -- Millane, --, therefor.

On Page 2, Col. 1 ("Other Publications"), Line 40, delete "Optic" and insert -- Optics --, therefor.

On Page 2, Col. 1 ("Other Publications"), Line 43, delete "Harley" and insert -- Hartley --, therefor.

On Page 2, Col. 2 ("Other Publications"), Line 11, delete "ultrafest" and insert -- ultrafast --, therefor.

On Page 2, Col. 2 ("Other Publications"), Line 50, after "transform" insert -- technique --.

In Col. 1, Line 5, after "CLAIM" insert -- OF --.

In Col. 10, Line 2, delete "-0.8 μm/V," and insert -- -0.8 pm/V, --, therefor.

In Col. 11, Line 28 (approx.), delete "$i\overline{U}_c(\omega) = \int u_c(t)e^{-j\omega t}dt$" -- and insert -- $\overline{U}_c(\omega) = \int u_c(t)e^{-j\omega t}dt$ --.

In Col. 14, Lines 14-15, delete "$E_{2\omega}(t)=u_{2\omega}(t)e^{j2\omega t}=\eta u_1(t)u_2(t)e^{j2\omega t}=\eta u_1(t)u_1(t-\tau)e^{j\omega\tau e^{j2\omega t}}$" and insert -- $E_{2\omega}(t)=u_{2\omega}(t)e^{j2\omega t}=\eta u_1(t)u_2(t)e^{j2\omega t}=\eta u_1(t)u_1(t-\tau)e^{-j\omega\tau}e^{j2\omega t}$. --, therefor.

In Col. 16, Line 1, delete " $\overline{A}_{PMT\_single}(\tau)$ " and insert -- $A_{PMT\_single}(\tau)$ --, therefor.

In Col. 16, Line 61 (approx.), after "knowledge of" delete "cos".

In Col. 17, Line 1, after "function" delete "cos".

In Col. 17, Line 41 (approx.), after " $|I^{Ha}_{symmetric}(f)|=|\overline{I}_{symmetric}(f)|=2|\overline{I}(f)|\ \cos(\varphi\ (f)-f\frac{\Delta t}{2}|$ " insert -- ) --.

In Col. 18, Line 17 (approx.), delete "$u_s(t)=\tilde{u}_s(t)e^{j\omega}{}_c{}^t$" and insert -- $u_s(t)=\tilde{u}_s(t)\ e^{j\omega_c t}$ --, therefor.

UNITED STATES PATENT AND TRADEMARK OFFICE
CERTIFICATE OF CORRECTION

PATENT NO.        : 7,133,134 B2
APPLICATION NO. : 10/357275
DATED             : November 7, 2006
INVENTOR(S)       : Aydogan Ozcan et al.

It is certified that error appears in the above-identified patent and that said Letters Patent is hereby corrected as shown below:

In Col. 19, Line 37 (approx.), delete "$u_{total}(t)=(\tilde{u}_s(t)+\tilde{u}_s^*(-t-\Delta t))e^{j\omega_c t}$" and insert -- $u_{total}(t)=(\tilde{u}_s(t)\phantom{}^*_s(-t-\Delta t))e^{j\omega_c t}+\tilde{u}$ --, therefor.

In Col. 20, Line 4 (approx.), delete "(31)" and insert -- (32) --, therefor.

Add the following U.S. patent documents to the references cited on the patent grant as approved by Examiner Sang Nguyen on September 7, 2006:

| U.S. Patent No. 4,674,824 | 01/23/1987 | Goodman et al. |
| U.S. Patent No. 4,778,236 | 10/18/1988 | Miyawaki |
| U.S. Patent No. 5,053,696 | 10/01/1991 | Williamson et al. |
| U.S. Patent No. 5,071,249 | 12/10/1991 | Takahashi et al. |
| U.S. Patent No. 5,317,147 | 05/31/1994 | Dändliker et al. |
| U.S. Patent No. 5,986,798 | 11/16/1999 | Karlsson et al. |

Signed and Sealed this

Twelfth Day of February, 2008

JON W. DUDAS
*Director of the United States Patent and Trademark Office*